(12) United States Patent
Niddam-Hildesheim et al.

(10) Patent No.: US 7,423,153 B2
(45) Date of Patent: Sep. 9, 2008

(54) CRYSTALLINE FORMS OF GATIFLOXACIN

(75) Inventors: Valerie Niddam-Hildesheim, Even-Yeouda (IL); Shlomit Wizel, Petah Tiqva (IL); Greta Sterimbaum, Rishon-Lezion (IL); Ehud Amir, Tel Aviv (IL)

(73) Assignee: Teva Pharmaceutical Industries Ltd. (IL)

( * ) Notice: Subject to any disclaimer, the term of this patent is extended or adjusted under 35 U.S.C. 154(b) by 0 days.

(21) Appl. No.: 10/436,736

(22) Filed: May 12, 2003

(65) Prior Publication Data
US 2004/0009989 A1 Jan. 15, 2004

Related U.S. Application Data

(60) Provisional application No. 60/379,510, filed on May 10, 2002, provisional application No. 60/389,093, filed on Jun. 14, 2002, provisional application No. 60/401,672, filed on Aug. 6, 2002, provisional application No. 60/402,749, filed on Aug. 12, 2002, provisional application No. 60/409,860, filed on Sep. 10, 2002, provisional application No. 60/423,338, filed on Nov. 1, 2002, provisional application No. 60/432,961, filed on Dec. 12, 2002, provisional application No. 60/444,812, filed on Feb. 3, 2003, provisional application No. 60/448,062, filed on Feb. 15, 2003.

(51) Int. Cl.
*C07D 401/04* (2006.01)
*A61K 31/47* (2006.01)

(52) U.S. Cl. .................... 546/156; 514/312; 544/363

(58) Field of Classification Search ............. 546/156; 514/312; 544/363
See application file for complete search history.

(56) References Cited

U.S. PATENT DOCUMENTS

| 4,980,470 | A | * | 12/1990 | Masuzawa et al. ........ 544/363 |
| 4,997,943 | A | * | 3/1991 | Iwata et al. ............. 544/363 |
| 5,051,509 | A | * | 9/1991 | Nagano et al. ........... 546/156 |
| 5,880,283 | A | | 3/1999 | Matsumoto et al. |
| 6,413,969 | B1 | | 7/2002 | Raghavan et al. |

FOREIGN PATENT DOCUMENTS

| EP | 0 629 621 A | 12/1994 |
| EP | 0805156 A1 * | 12/1995 |
| EP | 0 805 156 A | 11/1997 |
| WO | WO 02 22126 | 3/2002 |
| WO | WO 02/22126 A1 * | 3/2002 |
| WO | WO 03/086402 | 10/2003 |

OTHER PUBLICATIONS

G.M. Wall, "Pharmaceutical Applications of Drug Crystal Studies," Pharmaceutical Manufacturing, vol. 3, No. 2, Feb. 1986, pp. 33-42.
J. Haleblian and W. McCrone, "Pharmaceutical Applications of Polymorphism," Journal of Pharmaceutical Sciences, vol. 58, No. 8, Aug. 1969, pp. 911-929.
J.K. Haleblian, "Characterization of Habits and Crystalline Modification of Solids and Their Pharmaceutical Applications," Journal of Pharmaceutical Sciences, vol. 64, No. 8, Aug. 1975, pp. 1269-1288.

* cited by examiner

*Primary Examiner*—James O. Wilson
*Assistant Examiner*—Paul V. Ward
(74) *Attorney, Agent, or Firm*—Kenyon & Kenyon LLP

(57) ABSTRACT

Provided are novel crystalline forms of gatifloxacin denominated forms A, B, C, D, E1, F, G, H, I, and J, and methods for their preparation. Also provided are methods for making known crystalline forms of gatifloxacin, in particular forms omega and T2RP.

13 Claims, 38 Drawing Sheets

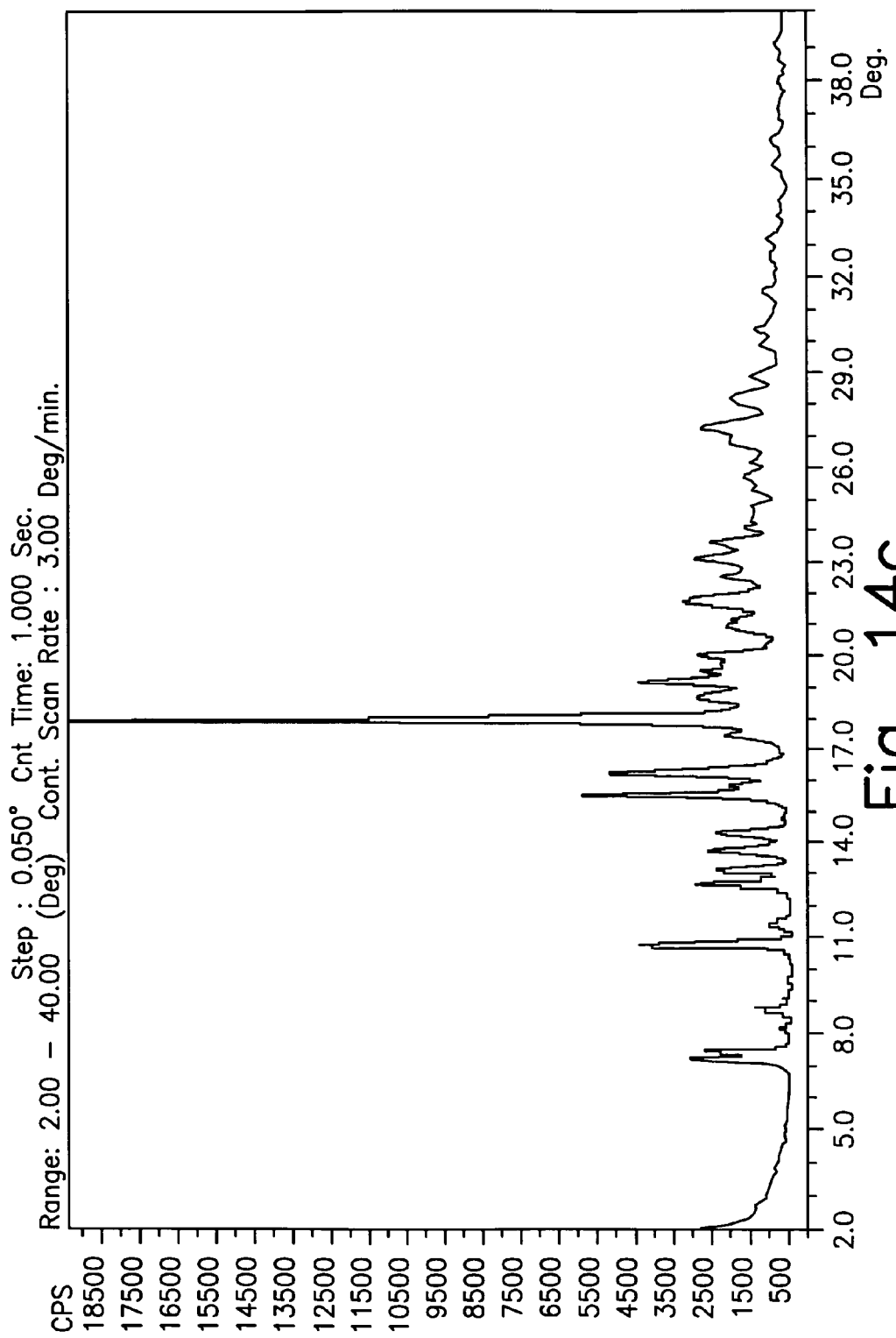

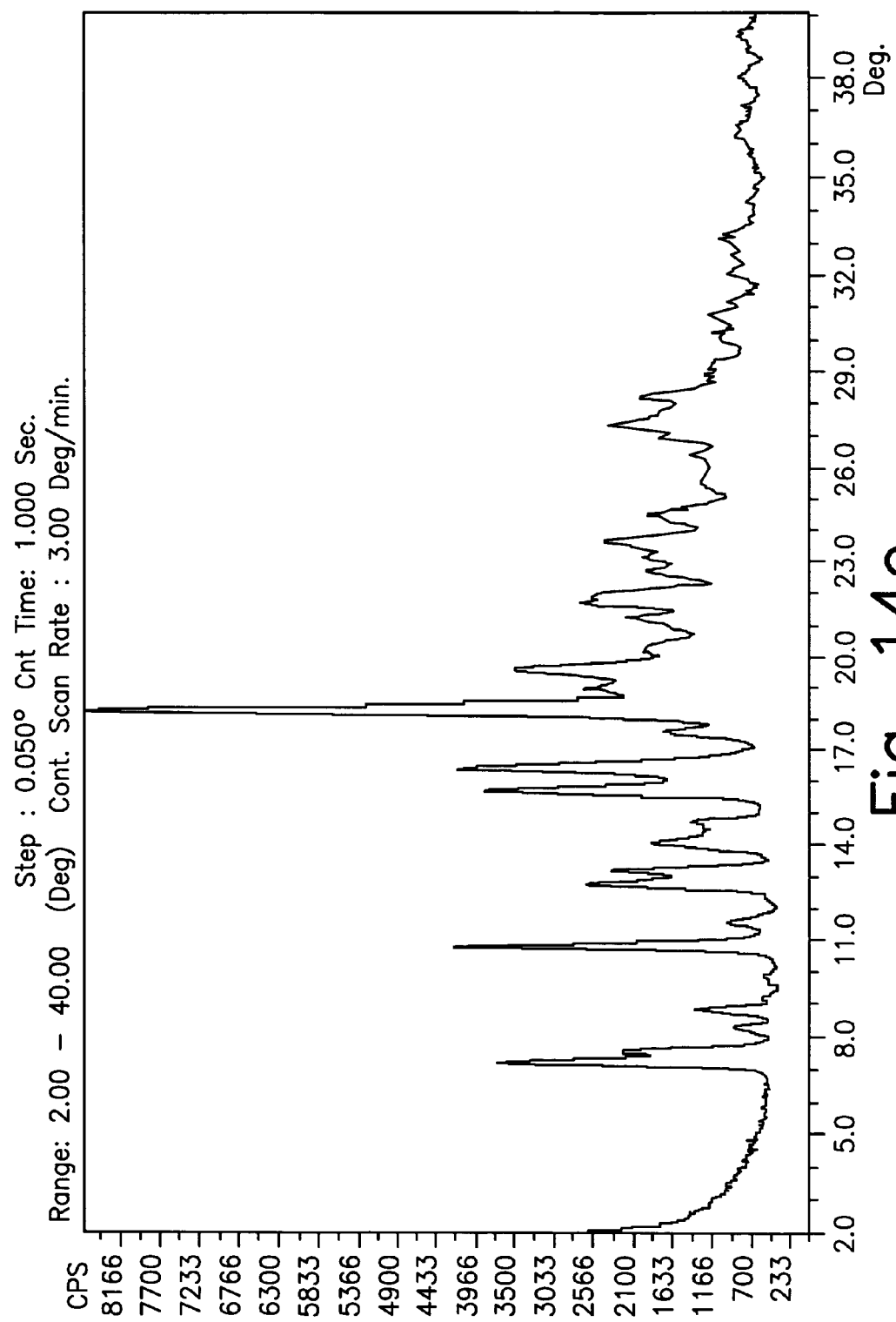

CRYSTALLINE FORMS OF GATIFLOXACIN

RELATED APPLICATIONS

The present application claims the benefit of the filing date of the following U.S. Provisional Patent Applications: 60/379,510, filed May 10, 2002; 60/389,093, filed Jun. 14, 2002; 60/401,672, filed Aug. 6, 2002; 60/402,749; filed Aug. 12, 2002; 60/409,860, filed Sep. 10, 2002; 60/423,338; filed Nov. 1, 2002; 60/432,961, Dec. 12, 2002; 60/444,812; filed Feb. 3, 2003; and 60/448,062, filed Feb. 15, 2003.

FIELD OF THE INVENTION

The present invent relates to novel polymorphs and pseudopolymorphs of (±) 1-cyclopropyl-6-fluoro-1,4-dihydro-8-methoxy-7-(3-methyl-1-piperazinyl)-4-oxo-3-quinolinecarboxylic acid, commonly known as gatifloxacin.

BACKGROUND OF THE INVENTION

Gatifloxacin, known as (±) 1-cyclopropyl-6-fluoro-1,4-dihydro-8-methoxy-7-(3-methyl-1-piperazinyl)-4-oxo-3-quinolinecarboxylic acid, has the following structure:

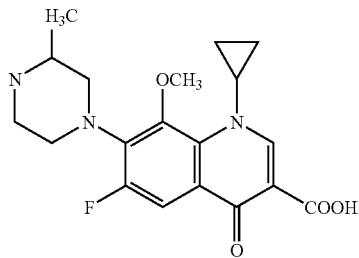

Gatifloxacin, an anti-bacterial agent, is marketed as Tequin® by Bristol-Myers Squibb. Tequin® is available in a dosage of 200 and 400 mg in the form of a vial or a tablet, which can be either injected or taken orally.

Many pharmaceutically active organic compounds can crystallize in more than one type of molecular packing with more than one type of internal crystal lattice. That is, the compounds crystallize in different crystalline forms. The respective resulting crystal structures (forms) can have, for example, different unit cells. This phenomenon—identical chemical structure but different internal structure—is referred to as polymorphism and the species having different molecular structures are referred to as polymorphs.

Many pharmacologically active organic compounds can also crystallize in crystalline forms such that second, foreign molecules, especially solvent molecules, are regularly incorporated into the crystal structure of the principal pharmacologically active compound. This phenomenon is sometimes referred to as pseudopolymorphism and the resulting structures as pseudopolymorphs. When the second molecule is a solvent molecule, the pseudopolymorphs can be referred to as solvates.

However, it is generally not possible to predict whether a particular organic compound will form different crystalline forms, let alone predict the structure and properties of the crystalline forms themselves.

The discovery of a new crystalline form of a pharmaceutically useful compound provides an opportunity to improve the performance characteristics of a pharmaceutical product. It enlarges the repertoire of materials that a formulation scientist has available for designing, for example, a pharmaceutical dosage form of a drug with a targeted release profile or other desired characteristic. It is clearly advantageous when this repertoire is enlarged by the discovery of new polymorphs or pseudopolymorphs of a useful compound. For a general review of polymorphs and the pharmaceutical applications of polymorphs see G. M. Wall, *Pharm Manuf.* 3, 33 (1986); J. K. Haleblian and W. McCrone, *J. Pharm. Sci.*, 58, 911(1969); and J. K. Haleblian, *J. Pharm. Sci.*, 64, 1269 (1975), all of which are incorporated herein by reference.

Crystalline forms can be influenced by controlling the conditions under which the compound is obtained in solid form. Solid state physical properties that can differ from one polymorph to the next include, for example, the flowability of the milled solid. Various crystalline forms can be more or less hygroscopic. Absorption of atmospheric moisture by compound in powder form can impede its ability to flow. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound that can vary from one polymorph or pseudopolymorph to the next is its rate of dissolution in aqueous media, e.g., gastric fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation, orientation, and packing of molecules in the unit cell, which characterize a particular polymorphic or pseudopolymorphic form of a substance. A polymorphic form may have thermodynamic properties different from those of the amorphous material or another polymorphic form. Thermodynamic properties can be used to distinguish between various polymorphs or pseudopolymorphs. Thermodynamic properties that can be used to distinguish between polymorphs and pseudopolymorphs can be measured in the laboratory by such techniques as capillary melting point, thermogravimetric analysis (TGA), differential scanning calorimetry (DSC), and differential thermal analysis (DTA).

A particular crystalline form can also possess distinct spectroscopic properties that may be detectable by, for example, solid state $^{13}C$ NMR spectroscopy and infrared (IR) spectroscopy. This is particularly so in the case of crystalline forms that are solvates because of the presence of absorptions or resonances due to the second, foreign molecule.

(±)-1-Cyclopropyl-6-fluoro-1,4-digydro-8-methoxy-7-(3-methyl-1-piperazinyl)-4-oxo-3-quinolenecarboxylic acid, commonly known as gatifloxacin, is a synthetic broad-spectrum antibacterial agent for oral or intravenous administration.

U.S. Pat. No. 5,880,283 discloses that gatifloxacin forms a hygroscopic hemihydrate. The hemihydrate (a pseudopolymorph) is reported to be easily formed upon crystallization of gatifloxacin from water-containing organic solvents. The hemihydrate reportedly has disadvantages for manufacturing of solid oral dosage forms, e.g., tablets. The patent further discloses a novel pseudopolymorph of gatifloxacin, the sesquihydrate, and presents thermal analysis and x-ray diffraction data for this material. The sesquihydrate is reported to be less hygroscopic and more stable in manufacturing.

U.S. Pat. No. 6,413,969 discloses at least 12 different polymorphs or pseudopolymorphs of gatifloxacin and discloses the x-ray powder diffraction diagrams of at least 10 of these. The hexahydrate, pentahydrate and sesquihydrate are crystallized directly from aqueous solvents. Other crystalline forms are crystallized from a molten phase or by solid-solid phase transformations. The pentahydrate form is, according to the disclosure of U.S. Pat. No. 6,413,969, the most thermodynamically stable form and has the lowest aqueous solubility at room temperature. The interrelationships between the twelve identified crystalline forms are given in the application.

SUMMARY OF THE INVENTION

In one aspect, the present invention the present invention relates to crystalline form of gatifloxacin, denominated form A, characterized by x-ray reflections at about 6.4°, 12.8°, 16.4°, 17.3°, and 19.4°±0.2° 2θ.

In another aspect the present invention relates to a crystalline form of gatifloxacin, denominated form B, characterized by x-ray reflections at about 9.2°, 10.6°, 11.9°, 18.4°, and 25.0°±0.2° 2θ; and to a method for making it, which method includes the steps of slurrying gatifloxacin in a lower alkanol selected from ethanol and 1-butanol at ambient temperature for a slurry time, especially about 8 to about 36 hours, and isolating crystalline form B of gatifloxacin from the slurry.

In another aspect, the present invention relates to crystalline form of gatifloxacin, denominated form C, having at least one characteristic selected from:
   a) x-ray reflections at about 7.2°, 10.8°, 15.8°, 21.8°, and 26.2°±0.2°2θ,
   b) DSC endotherms at about 173° and 177° C., and
   c) FTIR absorption bands at about 805, 1509, 1619, and 1728 cm$^{-1}$.

In a related aspect, the present invention relates to a method of making gatifloxacin form C including the step of heating either of gatifloxacin form B or form I at about 40° to about 70° C., especially 50° C, and atmospheric pressure for about 25 to about 48 hours.

In yet another aspect, the present invention relates to a crystalline form of gatifloxacin, denominated form D, characterized by x-ray reflections at about 8.2°, 14.4°, 19.0°, 21.4°, 21.9°, and 23.1°±0.2°2θ, and to a method of making it, which method includes the steps of slurrying gatifloxacin in methanol at ambient temperature for a slurry time, especially about 8 to about 36 hours, and isolating the crystalline form of gatifloxacin from the slurry.

In another aspect, the present invention relates to a method of making form D including the step of incubating gatifloxacin in vapors of methanol.

In a further aspect, the present invention relates to a crystalline form of gatifloxacin, denominated form F, characterized by x-ray reflections at 8.0°, 14.2°, 18.7°, 21.8°, and 23.0°±0.2° 2θ; and to a method of making it, which method includes the steps of
   a) providing a solution of gatifloxacin in a mixture of methanol and water, 90:10 (v:v),
   b) cooling the solution, especially to ambient temperature or below, especially about 5° C., and
   c) isolating the crystalline form of gatifloxacin.

In another aspect, the present invention relates to crystalline form of gatifloxacin, denominated form G, characterized by at least one of:
   a) x-ray reflections at about 17.2° and 17.6°±0.2° 2θ, and
   b) FTIR absorption bands at about 1614 cm$^{-1}$ and about 1267 cm$^{-1}$.

In a further aspect, the present invention relates to a method of making gatifloxacin crystalline form G including the step of drying either of gatifloxacin crystalline forms A or F at 50° C. and atmospheric pressure for at least about 20 hours.

In yet another aspect, the present invention relates to a crystalline form of gatifloxacin, denominated form H, characterized by x-ray reflections at about 6.6°, 13.2°, 19.6°, and 19.9°±0.2°2θ; and to a method of making it, which method includes the steps of:
   a) providing a solution of gatifloxacin in toluene, especially at reflux
   b) cooling the solution, especially to ambient temperature or below, especially about −5° C., and
   c) isolating the crystalline form of gatifloxacin.

In another aspect, the present invention relates to gatifloxacin toluene solvate.

In another aspect, the present invention relates to a method of making gatifloxacin crystalline form H including the steps of:
   a) slurrying gatifloxacin in toulene at ambient temperature for a slurry time, especially about 8 to about 36 hours, and
   b) isolating the crystalline form of gatifloxacin from the slurry.

In a further aspect, the present invention relates to a crystalline form of gatifloxacin, denominated form I, characterized by x-ray reflections at 6.5°, 7.1°, 12.8°, 17.2°, 19.3°, and 21.0°±0.2°, and to a method of making it, which method includes the steps of:
   a) providing a solution of gatifloxacin in 1-butanol, especially at reflux
   b) cooling the solution, especially to ambient temperature or below, especially about −5°, and
   c) isolating the crystalline form of gatifloxacin from the suspension.

In still yet another aspect, the present invention relates to a crystalline form of gatifloxacin that exists in various solvated forms, denominated form J, characterized by a x-ray reflection at about 6.7°, 11.3°, 13.8°, and 16.4°±0.2° 2θ. Form J can exist at least as an iso-propanol solvate, that can be made by an incubation process or a crystallization process; a methyl ethyl ketone solvate that can be made by an incubation process; an acetone solvate that can be made by an incubation process or slurry process; a 1-butanol solvate that can be made by a crystallization process; or as a tetrahydrofuran solvate that can be made by a slurry process.

In still yet another aspect, the present invention relates to a crystalline form of gatifloxacin, denominated form E1, characterized by x-ray reflections at about 7.1°, 7.3°, 10.8°, 15.7°, 16.4°, and 18.1°±0.2° 2θ; and to methods for making it. Form E1 contains acetonitrile, water, or a mixture of acetonitrile and water at up to about 10 wt %.

In another aspect, the present invention relates to a crystalline form of gatifloxacin, E1-ACN, and to methods of making it. E1-ACN has the crystallographic characteristics of E1, namely x-ray reflections at about 7.1°, 7.3°, 10.8°, 15.7°, 16.4°, and 18.1°±0.2° 2θ; and contains up to about 10% acetonitrile.

Gatifloxacin E1-ACN can be made by a process including the steps of:
   a) providing a solution of gatifloxacin in acetonitrile having about 5 wt % or less water, especially about 4.5 wt % or less water, at reflux, b) cooling the solution to a seeding temperature of about 57° to 70° C., especially about 60° C., c) seeding the solution at the seeding temperature and, optionally, maintaining the seeded solution at the seeding temperature for a seeding time of about 30 minutes or more, d) cooling the seeded solution, especially to ambient temperature or below, especially 5° C. or below, and e) isolating the crystalline E1-ACN gatifloxacin.

In still a further aspect, the present invention relates to a hydrate form E1 having a water content of about 7.5 to about 10 weight percent (wt %). In a particular aspect, the present invention relates to a hydrated form of gatifloxacin that is a dihydrate (E1 dihydrate) having about 9.3 weight percent water. The hydrated E1 of the present invention, regardless of water content, is substantially free of prior-art sesquihydrate and is characterized by x-ray reflections at about 7.1°, 7.3°, 10.8°, 15.7°, 16.4°, and 18.1°±0.2° 2θ.

In a further aspect, the present invention relates to methods of making hydrated E1, which method includes the step of treating gatifloxacin form E1-ACN solvate with a moist gas, especially moist gas of about 55% to about 75% relative humidity at a temperature from ambient temperature to about 60° C., especially about 20° to 30° C.; although treating at 50° C. can be advantageous.

In still a further aspect, the present invention relates to a method of making prior-art crystalline form of gatifloxacin, denominated form omega (Ω), including the steps of:

a) providing, at reflux, a filtered solution of gatifloxacin in acetonitrile, wherein the solution has a water content of about 5% or less, especially about 4.5 wt % or less, b) cooling the solution to a seeding temperature of about 50° to about 56° C.

c) seeding the solution with gatifloxacin at the seeding temperature and, optionally, maintaining the seeded solution at the seeding temperature for a seeding time of at least about 30 minutes, d) cooling the seeded solution, especially to ambient temperature or below, especially about 5° C., and e) isolating the crystalline gatifloxacin crystalline form omega from the suspension.

In still a further aspect, the present invention relates to method of making prior-art crystalline form of gatifloxacin T2RP. In one such method, >200 g (especially >1000 g) of gatifloxacin E1-ACN are slurried with ethanol and the solid isolated from the slurry is treated with moist gas, especially in a fluidized bed apparatus. Other methods including the step of treating novel forms of gatifloxacin are also disclosed.

In another aspect, the present invention relates to a method of making about 200 g or less of gatifloxacin form T2RP including the steps of slurrying about 200 g or less of gatifloxacin E1-ACN in ethanol, isolating the solid from the slurry, and drying the isolated solid at about 50° C.

In another aspect, the present invention relates to gatifloxacin having an average particle size less than about 100μ, especially less than about 50μ, wherein the gatifloxacin is in a crystalline form selected from forms A, B, C, D, hydrated E1, F, G, H, I, and J.

In yet still another aspect, the present invention relates to pharmaceutical compositions containing a hydrated form of gatifloxacin form E1, especially E1 dihydrate, that are substantially free of sesquihydrate.

BRIEF DESCRIPTION OF THE DRAWINGS

FIG. 14a through 14g show representative x-ray diffraction diagrams of gatifloxacin form E1.

DETAILED DESCRIPTION OF THE INVENTION

Figure 1:
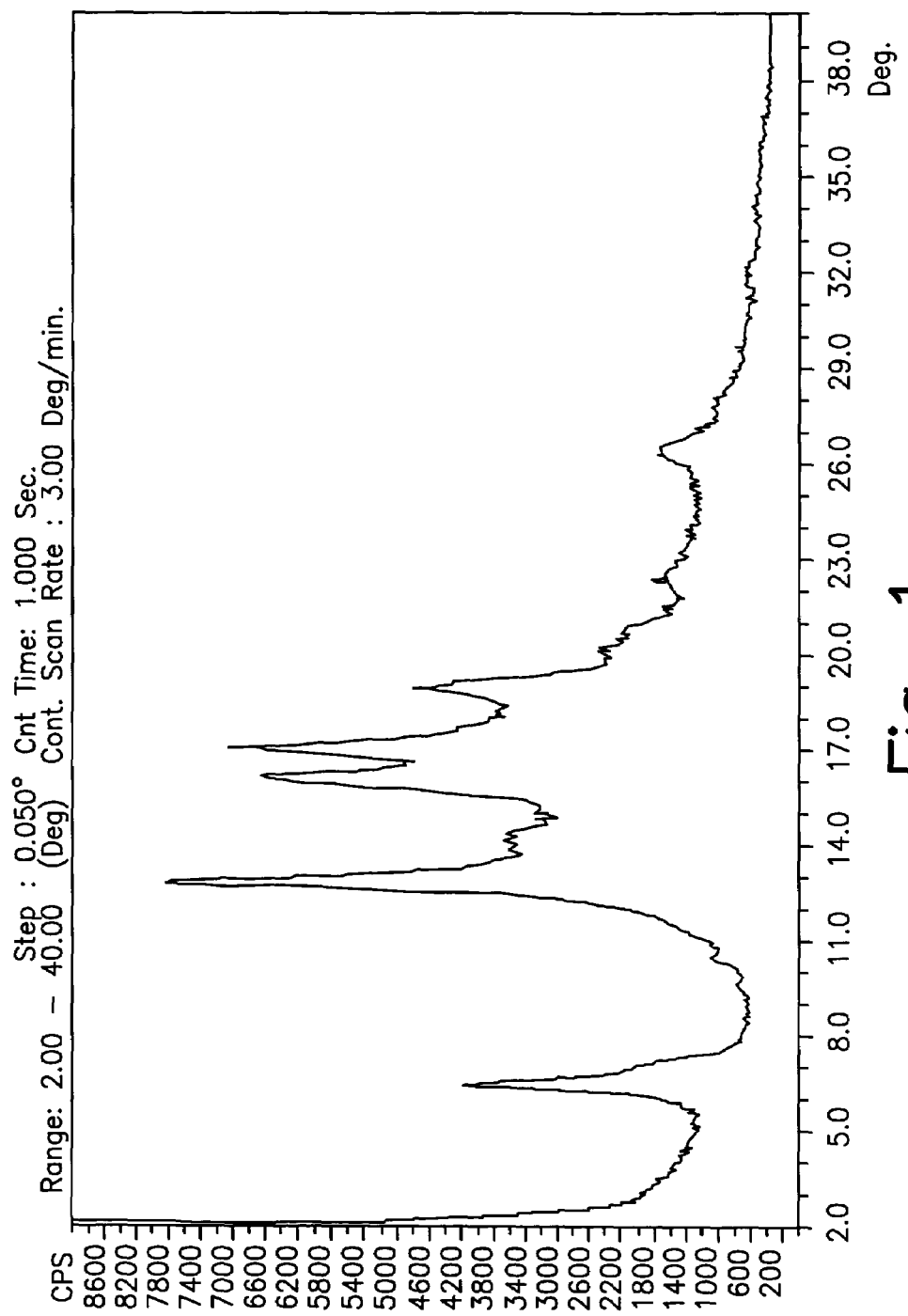
FIG. 1 shows a representative x-ray diffraction diagram of gatifloxacin form A.

Gatifloxacin, (±) 1-cyclopropyl-6-fluoro-1,4-dihydro-8-methoxy-7-(3-methyl-1-piperazinyl)-4-oxo-3-quinolinecarboxylic acid, is a known anti-bacterial. The present invention provides novel crystalline forms (polymorphs, pseudopolymorphs) of this useful drug.

Unless otherwise specified or required by the context, gatifloxacin refers to the compound in any crystalline form, which may or may not be a solvated crystalline form, or in an amorphous form.

As used herein, gatifloxacin form omega (i), form T1RP, and form T2RP refer to the crystalline forms disclosed under those designations in U.S. Pat. No. 6,413,969. Gatifloxacin sesquihydrate refers to the crystalline form of gatifloxacin denominated as such in U.S. Pat. No. 5,880,283.

As used herein, the phrase, "having at least one characteristic of GTF form '#'," where "#" is an arabic letter or numeral or a roman numeral, or any combinatiuon of these denoting a crystalline form of gatifloxacin, refers to a crystalline form of gatifloxacin that exhibits at least the characteristic powder x-ray diffraction (PXRD) reflections (or peaks), or the characteristic DSC endo- or exotherms, or, where applicable, the characteristic FTIR absorption bands of form '#'.

As used herein in connection with a measured quantity, the term, "about," refers to that variation in the measured quantity as would be expected by the skilled artisan making the measurement and exercising a level of care commensurate with the objective of the measurement and the precision of the measuring equipment used.

As used herein, the term ambient temperature is a temperature between about 18° and about 30° C.

As used herein, ambient pressure is about 760 mmHg.

As used herein in connection with drying procedures, drying under vacuum (in vacuo) implies drying at a reduced pressure of about 10 to about 20 mm Hg.

As used herein in connection with a multi-component mixture of liquids, the term % v/v refers to the ratio of the volume of the named component to the sum of the volumes of all components used to make the mixture, times 100. Thus, a mixture of approximately equal volumes of A and B is referred to as "50 vol-% A" (or 50 vol-% B). Alternatively, this mixture can be referred to as "a mixture of A and B, 50:50 (v:v)".

As used herein, lower alkanol refers to an alcohol of formula $C_nH_{2n+1}OH$, where n is 6 or less.

X-ray reflections reported herein were determined by the powder diffraction technique (PXRD). X-ray powder diffraction analysis was performed using a Scintag powder diffractometer with variable goniometer, a Cu source, and a solid state detector. A standard round aluminum sample holder with zero background quartz plate was used. Samples were scanned from 2° to 40° 2θ at 3° per minute. Reflections are reported as peak maxima in the Intensity vs. 2θ plots, and are subject to the normal experimental error (uncertainty) of ±0.2°. Wet samples were promptly analyzed "as is," i.e., without drying or grinding prior to the analysis.

Fourier transform infra-red spectra (FTIR) were obtained on Nujoll mulls using a Perkin Elmer SpectrumOne spectrophotometer. Sixteen scans were recorded from 4000 to 400 $cm^{-1}$ at a resolution of 4 $cm^{-1}$.

Differential scanning calorimetric (DSC) analysis was performed with a Mettler Toledo DSC 821$^e$ calorimeter. Samples of about 3 to about 5 milligrams, held in a vented (3-hole) crucible, were analyzed at a heating rate of 10° per minute.

Thermogravimetric analysis (TGA) was performed using a Mettler TG50 thermobalance. Samples of 7 to 15 milligrams were analyzed at a heating rate of 10° C. per minute in the temperature range between about 25° C. and about 200° C.

The water content (wt-% water) of crystalline forms of gatifloxacin reported herein was determined by the Karl-Fisher method. Water content of solutions was likewise determined by the Karl-Fisher method.

In particular embodiments, a novel crystalline form of the present invention is made by a crystallization (precipitation) process in which a particular crystalline form of gatifloxacin is crystallized from a solution in an organic solvent. The solvent can be a single component (i.e., a single organic compound normally liquid at ambient temperature), or it can be multi-component (i.e., a mixture of organic compounds normally liquid at ambient temperature). One of the components of a multi-component solvent can be a poor solvent for gatifloxacin. Crystallization can be induced by changing the solubility of gatifloxacin in the solvent. The solubility can be altered by, for example, lowering the temperature of the solution, or by adding an "anti-solvent" to the solution.

In particular embodiments, filtration of the solution from which the crystalline form of gatifloxacin is to be crystallized has been found to be an important step. Although an understanding of the theory of the importance of this filtration step is unnecessary to the practice of the present invention, the present inventors speculate that filtration, especially hot filtration, removes and promotes control of the temperature at which nucleation can be sustained and crystallization begins. Both of these are parameters capable of influencing the crystalline form of gatifloxacin obtained.

The temperature of the solution can be lowered in one or more steps. For making certain crystalline forms, it is advantageous to lower the temperature in steps and to maintain the temperature at each step for a holding time (i.e., a first holding time at the temperature at the end of the first cooling step, a second holding time at the temperature at the end of the second cooling step, etc.). Step-wise lowering of the temperature can be advantageous when seeding is employed. Seeding is a well-known technique for inducing crystallization of a compound from its solution. When seeding is employed, the solution is cooled into a seeding temperature in a first cooling step. The temperature at which the solution is seeded is denoted the seeding temperature and the holding time at that temperature is known as a seeding time. It is sometimes necessary to carefully control the cooling rate of any cooling step, depending on the crystalline form of gatifloxacin being sought.

The skilled artisan will appreciate that in any method of the present invention in which a solution of gatifloxacin is provided, the solution can be provided by any means; for example by dissolving gatifloxacin in the solvent or, where the solvent does not interfere with the reaction, by preparing gatifloxacin in the presence of the desired solvent, or in the presence of one component of a multi-component solvent system whereafter other component(s) are introduced.

An anti-solvent is an organic compound, normally a liquid at ambient temperature, that is a poor solvent for the compound to be crystallized (here gatifloxacin). The solubility of the compound to be crystallized from the combination of solvent and anti-solvent is lower than the solubility of the compound in the original solvent. In particular embodiments, crystallization is induced through use of an anti-solvent and by lowering the temperature of the solution.

The crystalline form of gatifloxacin is then isolated by standard means.

In other embodiments, a novel crystalline form of gatifloxacin of the present invention is made in a slurry (suspension) process in which gatifloxacin is slurried (suspended), with agitation, in a slurry solvent, usually at ambient temperature, for a slurry time. As long as there is sufficient slurry solvent to wet and suspend the gatifloxacin, the ratio of gatifloxacin to slurry solvent is not critical and will be dictated by practical considerations, for example, ease of handling. The slurry time is not critical and will usually be between about 8 and about 36 hours. The skilled artisan will know to adjust the slurry time by routine optimization by, for example, isolating the solid from a small aliquot of the slurry and determining the crystalline form of the solid by an appropriate technique, for example x-ray diffraction, differential scanning calorimetry, or Fourier transform infra-red spectroscopy.

At the end of the slurry time, the crystalline form of gatifloxacin is isolated by standard techniques, for example filtration (gravity or suction) or centrifugation, to mention just two.

In other embodiments, a novel crystalline form of gatifloxacin of the present invention is made by treating a vapor incubation process wherein gatifloxacin is exposed to (i.e., incubated with) vapors of an organic solvent, usually at ambient temperature, for an incubation time. Any suitable chamber capable of holding the sample and containing the solvent vapors can be used. The incubation time is not critical and will generally be between about 2 and about 20 days.

In those embodiments that yield a crystalline form of gatifloxacin that is a solvate, care should be taken to analyze the material without drying that might remove the solvent.

One or more of the foregoing methods, and other methods such as thermal treatment (heating, drying) described hereinbelow, are adapted to the preparation of the novel crystalline forms of gatifloxacin of the present invention.

Figure 2:
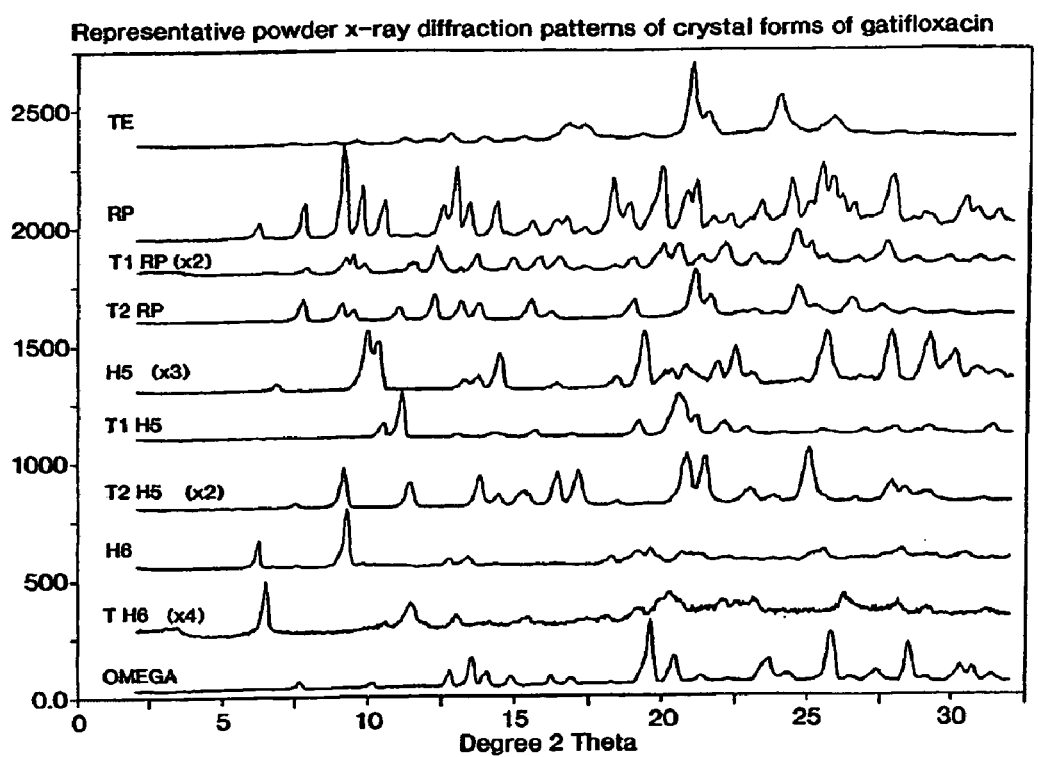
FIG. 2 shows a representative DSC thermogram of gatifloxacin form A.
Figure 3:
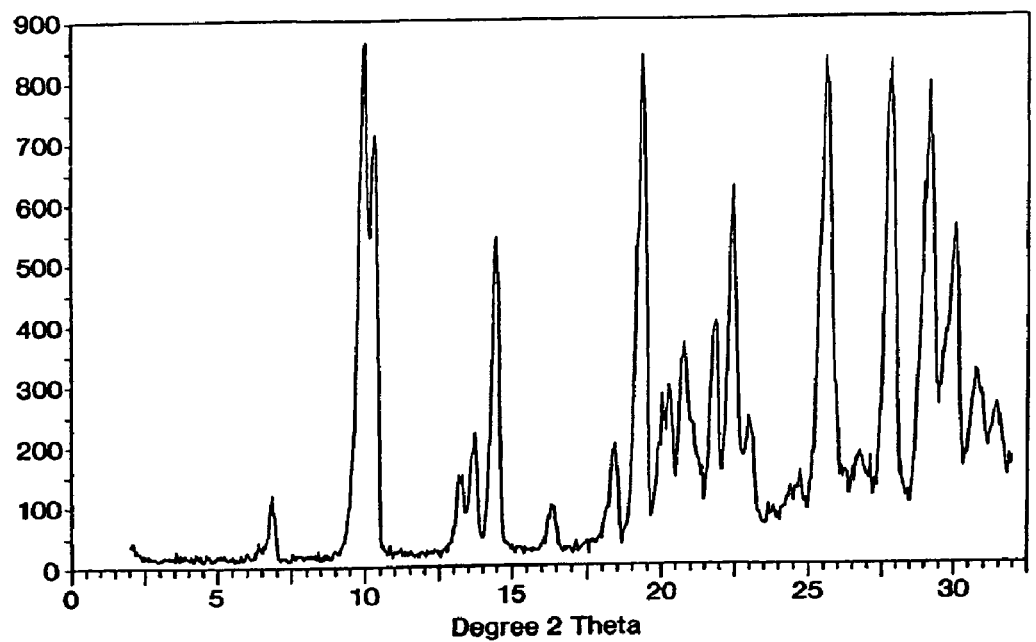
FIG. 3 shows a representative TGA thermogram of gatifloxacin form A.

In one embodiment, the present invention provide a crystalline form of gatifloxacin, denominated form A, which is characterized by x-ray reflections at about 6.4°, 12.8°, 16.4°, 17.3°, and 19.4°±0.2° 2θ. A typical x-ray diffraction diagram of form A is shown in FIG. 1. A typical DSC thermogram of form A is shown in FIG. 2. The loss on drying of form A, as determined by TGA, can be as high as 65%. A typical TGA thermogram of form A is shown in FIG. 3.

Form A can be made by a slurry process including the steps of slurrying gatifloxacin in iso-propanol (IPA) at ambient temperature and isolating the crystalline form A.

Form A can be converted to form J by, for example, drying at 50° C. The skilled artisan will know to adjust the drying time according to, for example, sample size and drying equipment used. Generally, a time of about 12 to about 18 hours is sufficient to effect the conversion.

Figure 4:
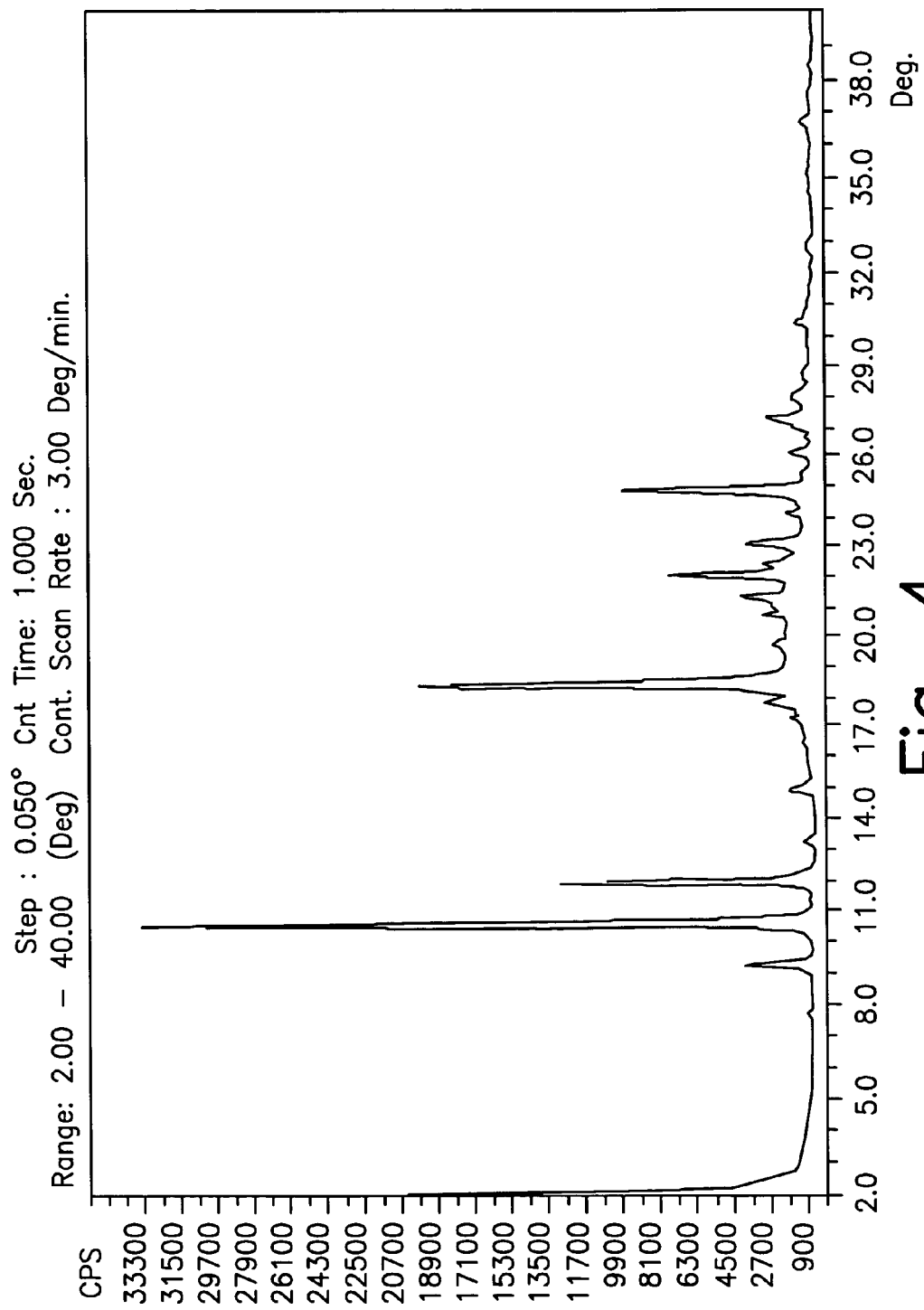
FIG. 4 shows a representative x-ray diffraction diagram of gatifloxacin form B.
Figure 5:
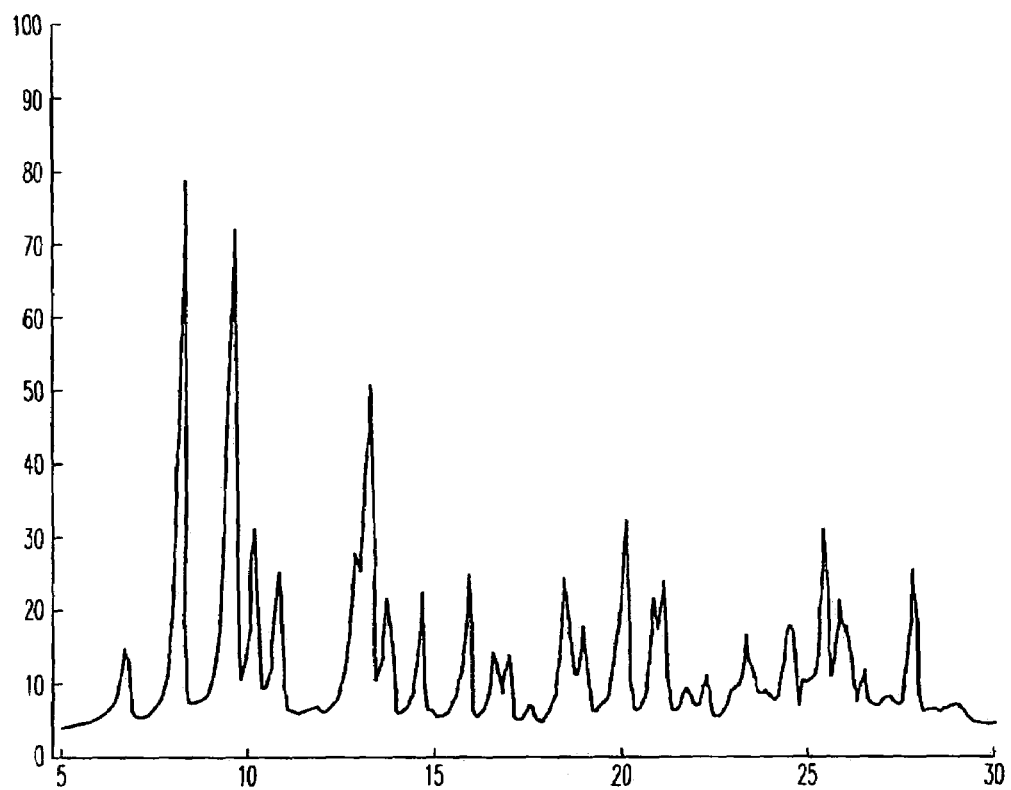
FIG. 5 shows a representative DSC thermogram of gatifloxacin form B.
Figure 6:
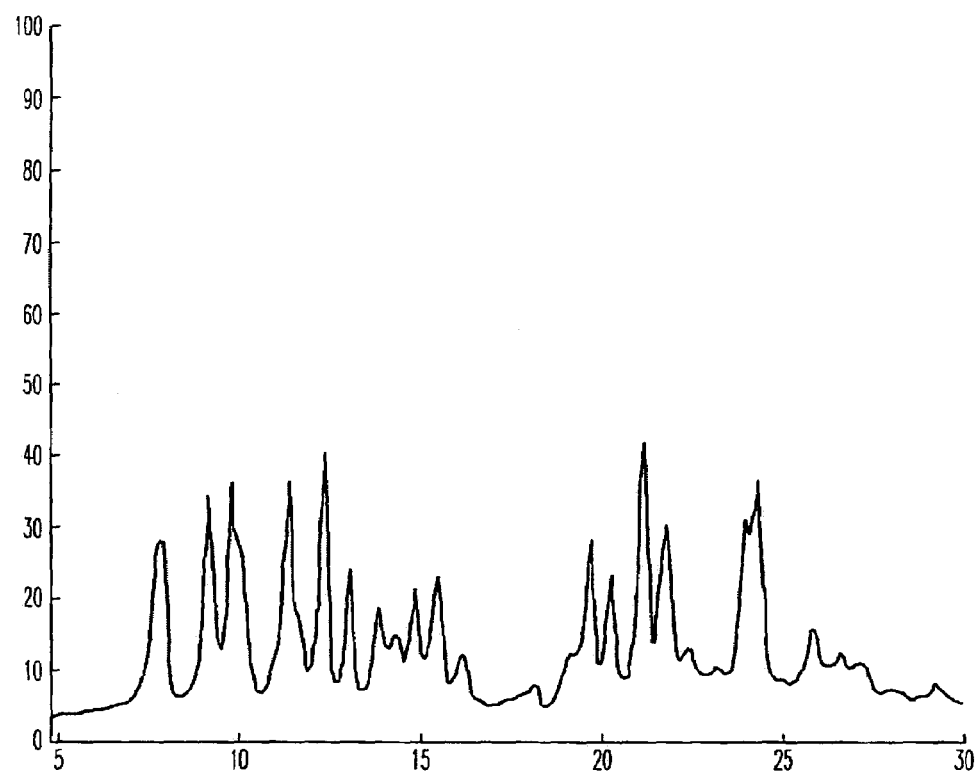
FIG. 6 shows a representative TGA thermogram of gatifloxacin form B.

In another embodiment, the present invention provides a novel crystalline form of gatifloxacin, denominated form B, characterized by x-ray diffraction reflections at 2θ=9.2°, 10.6°, 11.9°, 18.4°, and 25.0°. A typical x-ray diffraction diagram for form B is shown in FIG. 4. A typical DSC thermogram of form B is shown in FIG. 5. A typical TGA thermogram of form B is shown in FIG. 6.

Gatifloxacin crystalline form B can be made in a slurry process including the steps of slurrying gatifloxacin at ambient temperature in either 1-butanol or ethanol and recovering the gatifloxacin form B.

In still another embodiment, the present invention provides a novel crystalline form of gatifloxacin, denominated form C, that can be characterized by one or more of
a) x-ray reflections at about 7.2°, 10.8°, 15.8°, 21.8°, and 26.2°±0.2°2θ,
b) DSC endotherms at about 173° and 177° C., and
c) FTIR absorption bands at about 805, 1509, 1619, and 1728 $cm^{-1}$.

Figure 7:
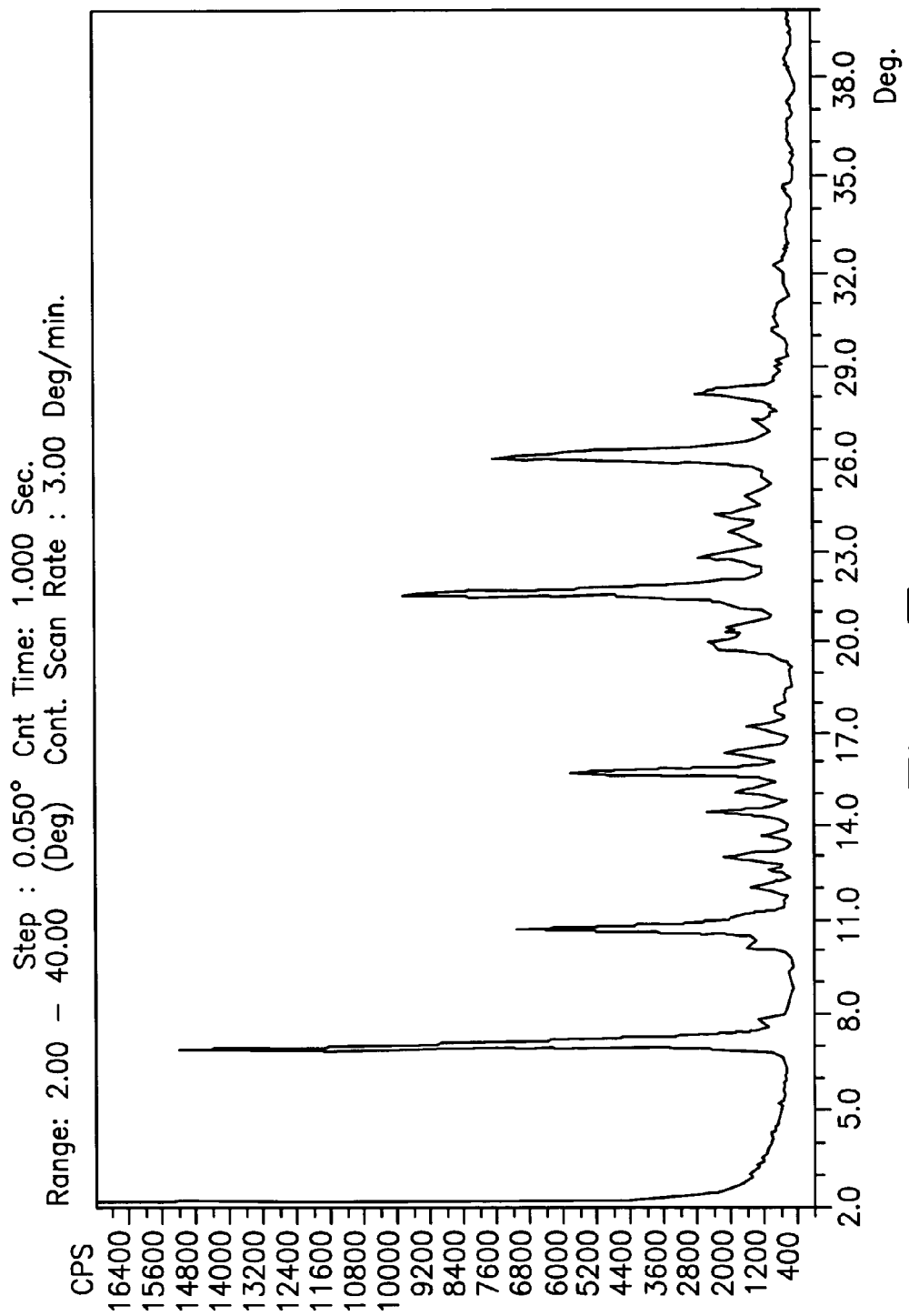
FIG. 7 shows a representative x-ray diffraction diagram of gatifloxacin form C.
Figure 8:
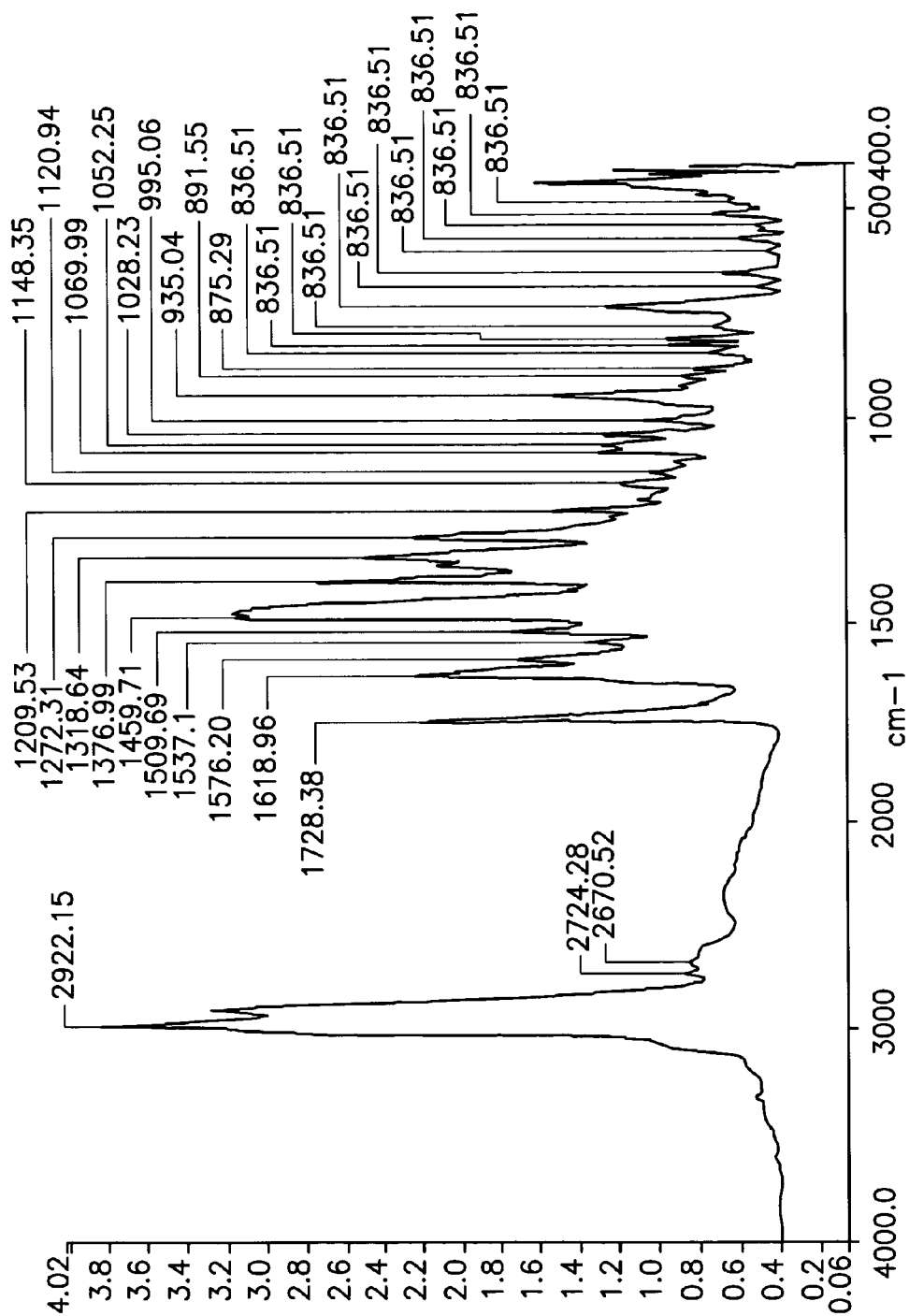
FIG. 8 shows a representative FTIR spectra for gatifloxacin form C.
Figure 9:
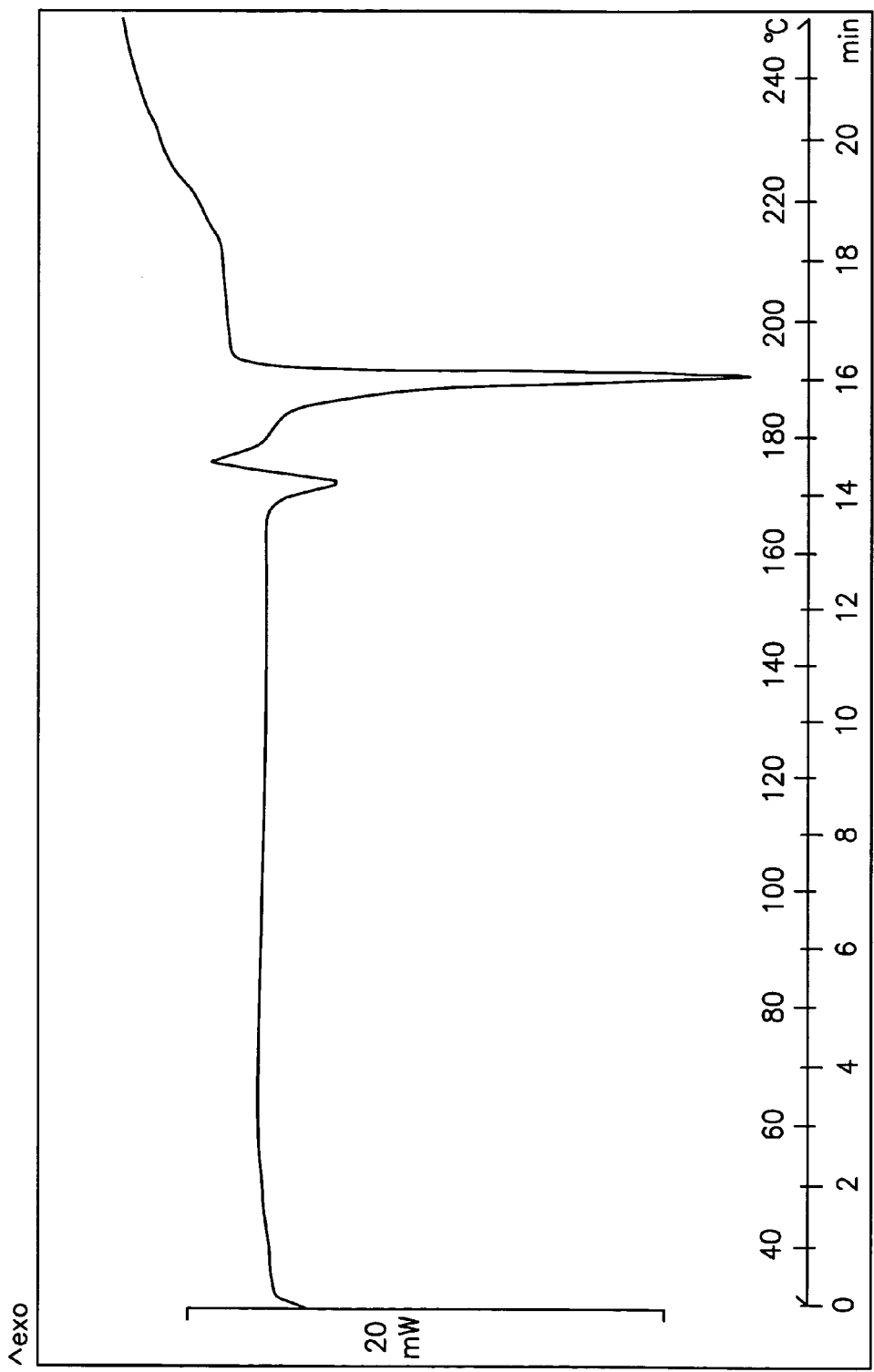
FIG. 9 shows a representative DSC thermogram of gatifloxacin form C.
Figure 10:
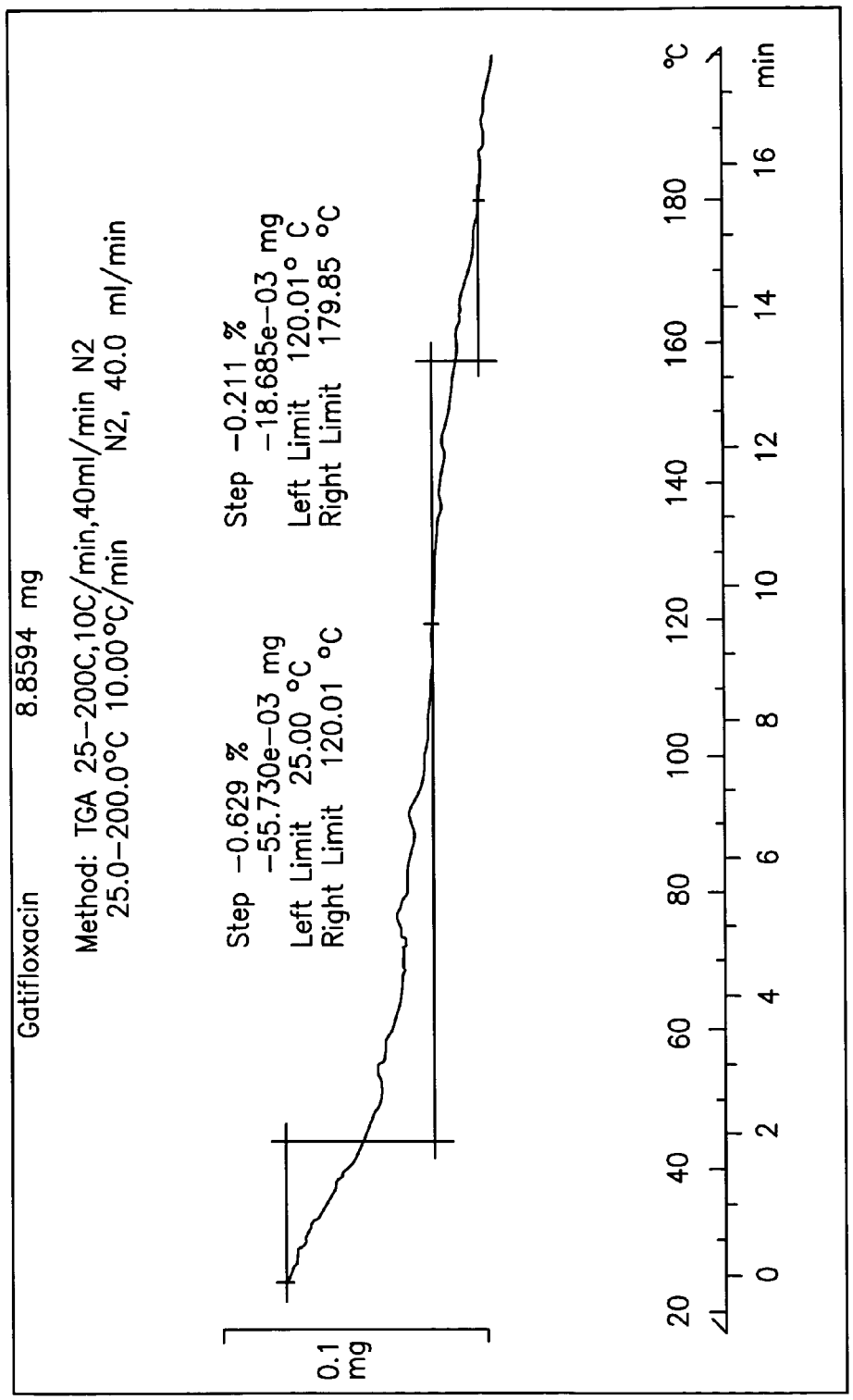
FIG. 10 shows a representative TGA thermogram of gatifloxacin form C.

A typical x-ray diffraction diagram of form C is shown in FIG. 7. A typical FTIR spectrum for form C is shown in FIG. 8. A typical DSC thermogram of form C is shown in FIG. 9. A typical TGA thermogram of form C is shown in FIG. 10.

Form C can be made by, for example, drying form B, described above, at ambient pressure and about 60° C., or at about 50° C. and 10 to 20 mm Hg. Form C can also be made by drying form I, described hereinbelow, at about 50° to about 60° C.

Figure 11:
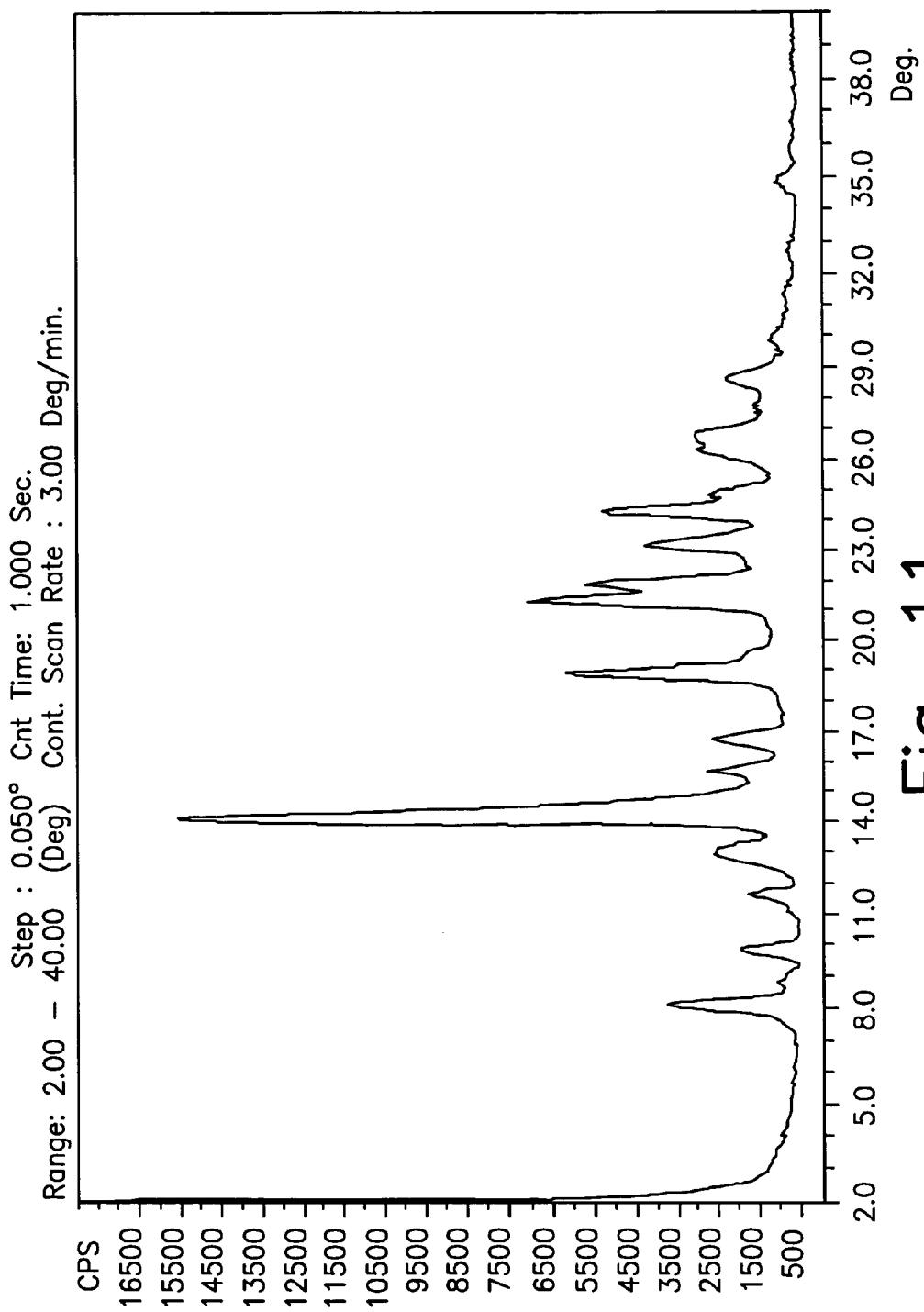
FIG. 11 shows a representative x-ray diffraction diagram of gatifloxacin form D.
Figure 12:
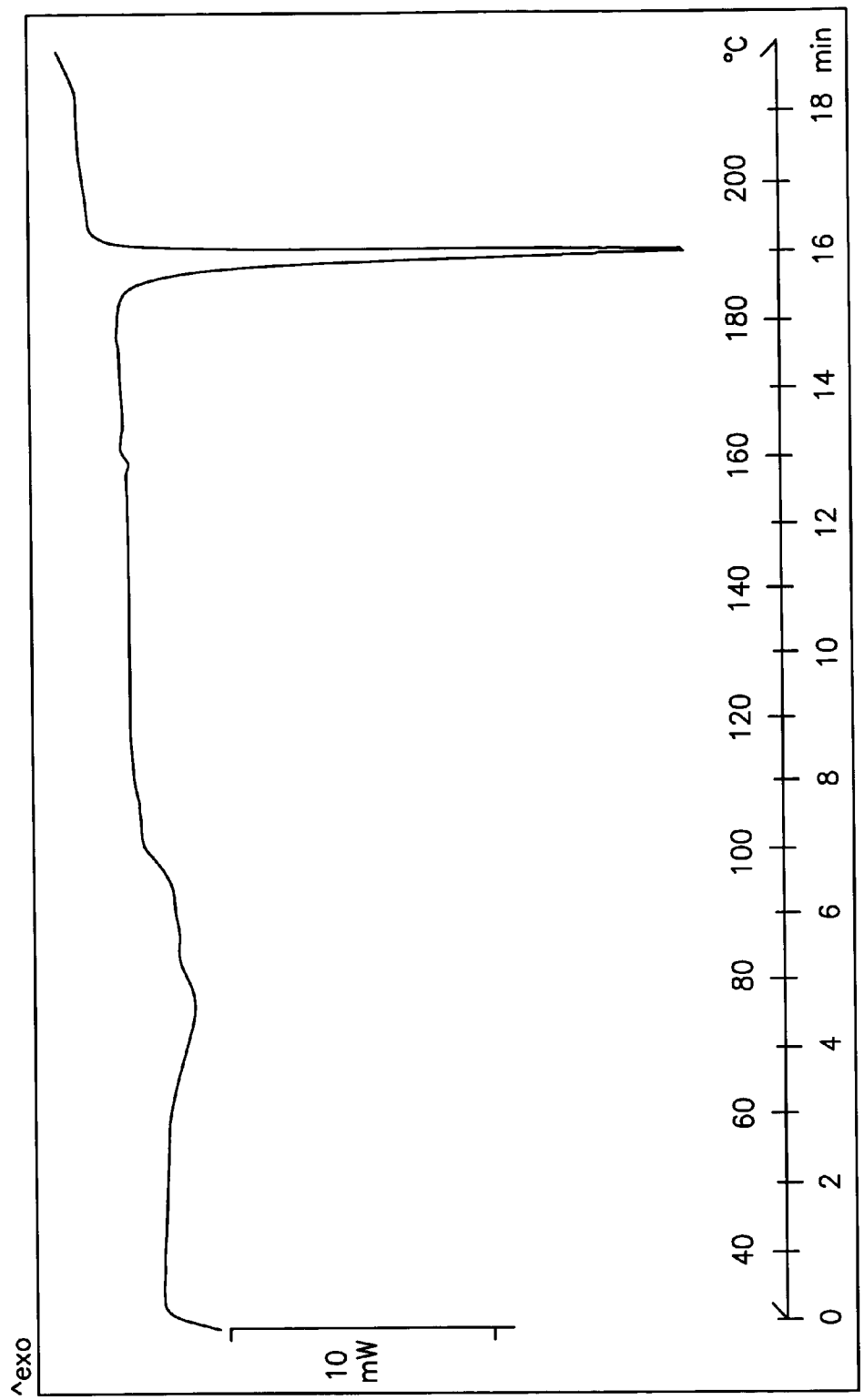
FIG. 12 shows a representative DSC thermogram of form D.
Figure 13:
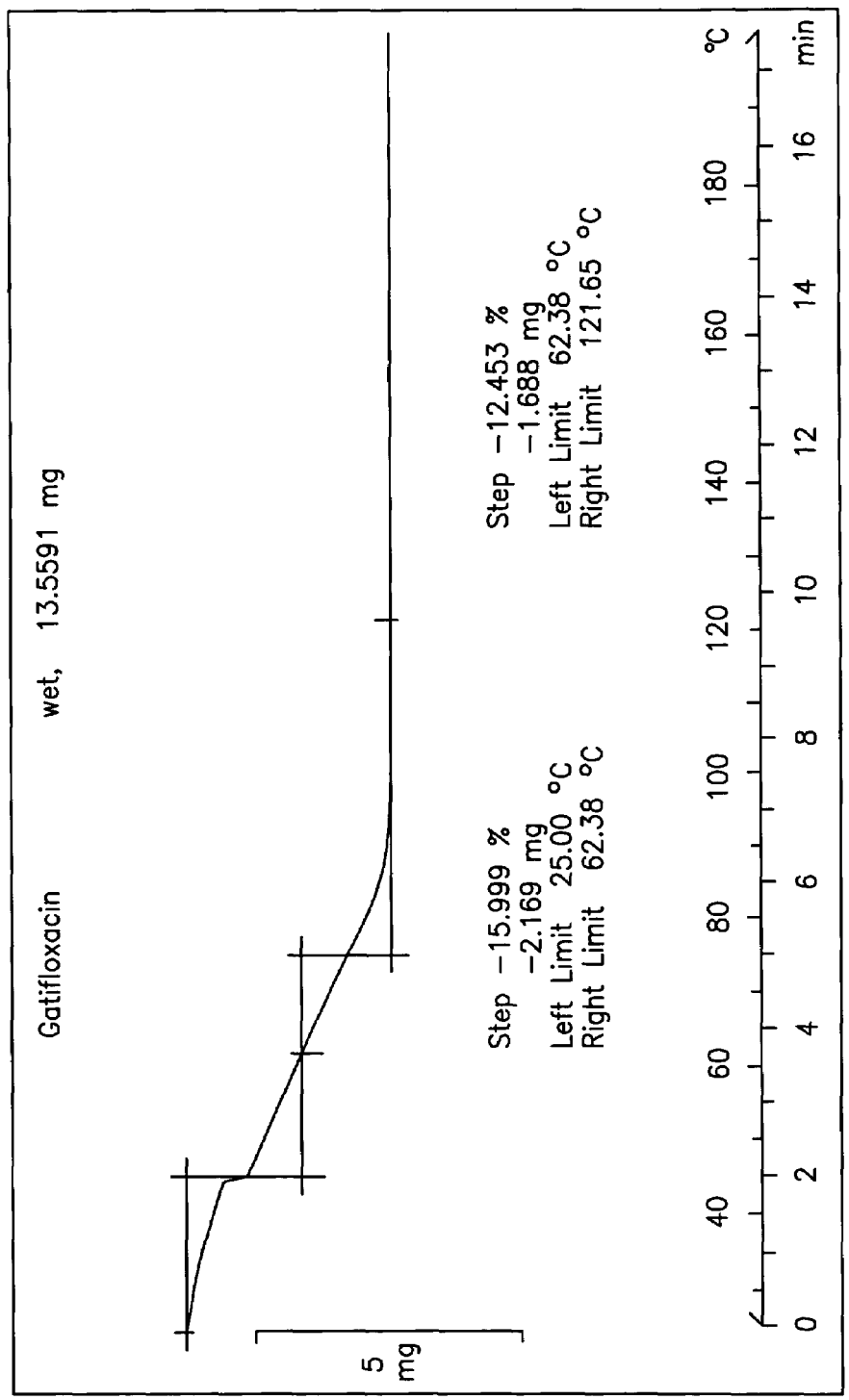
FIG. 13 shows a representative TGA thermogram of form D.
Figure 14A:
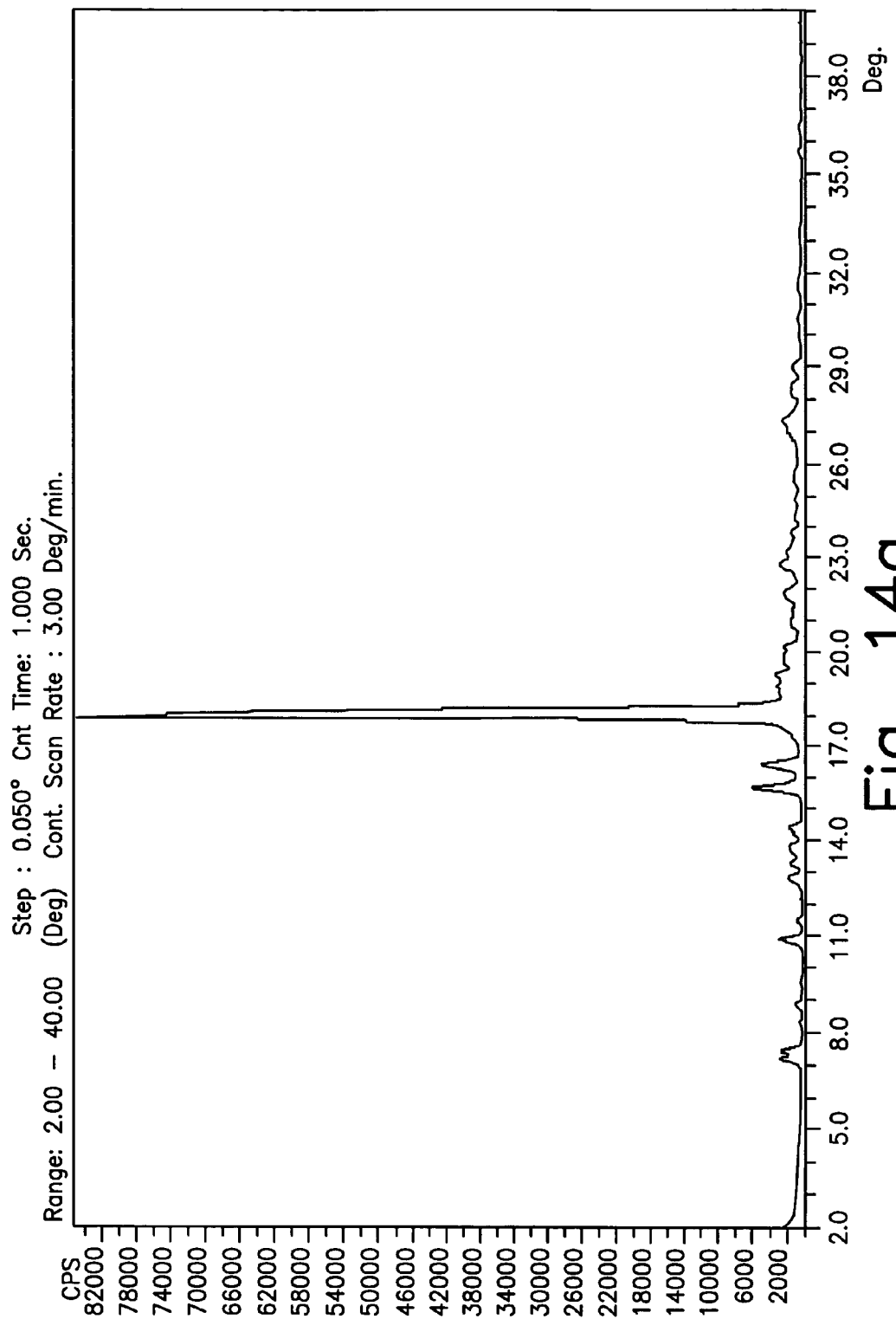
Figure 14B:
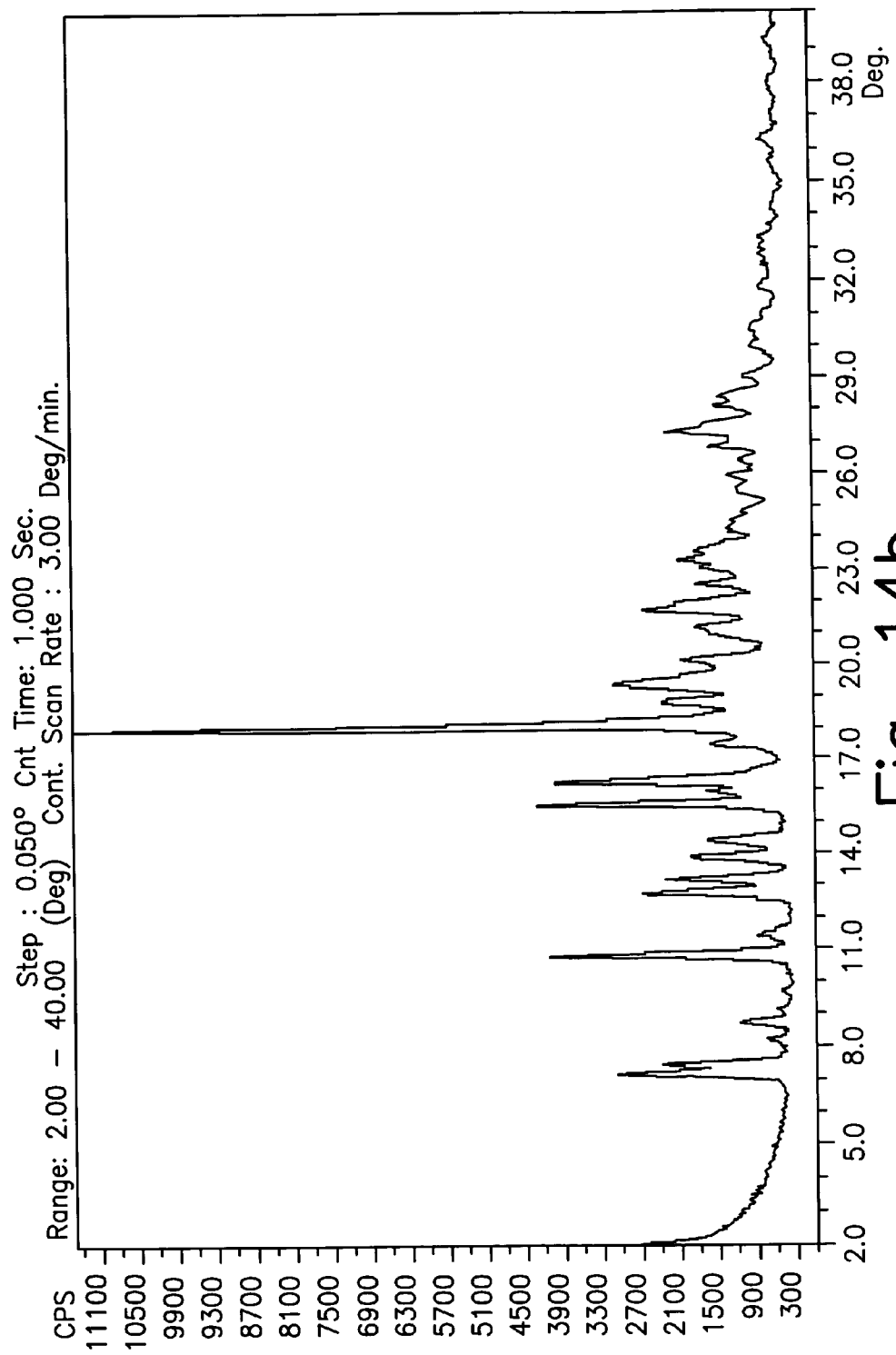
Figure 14D:
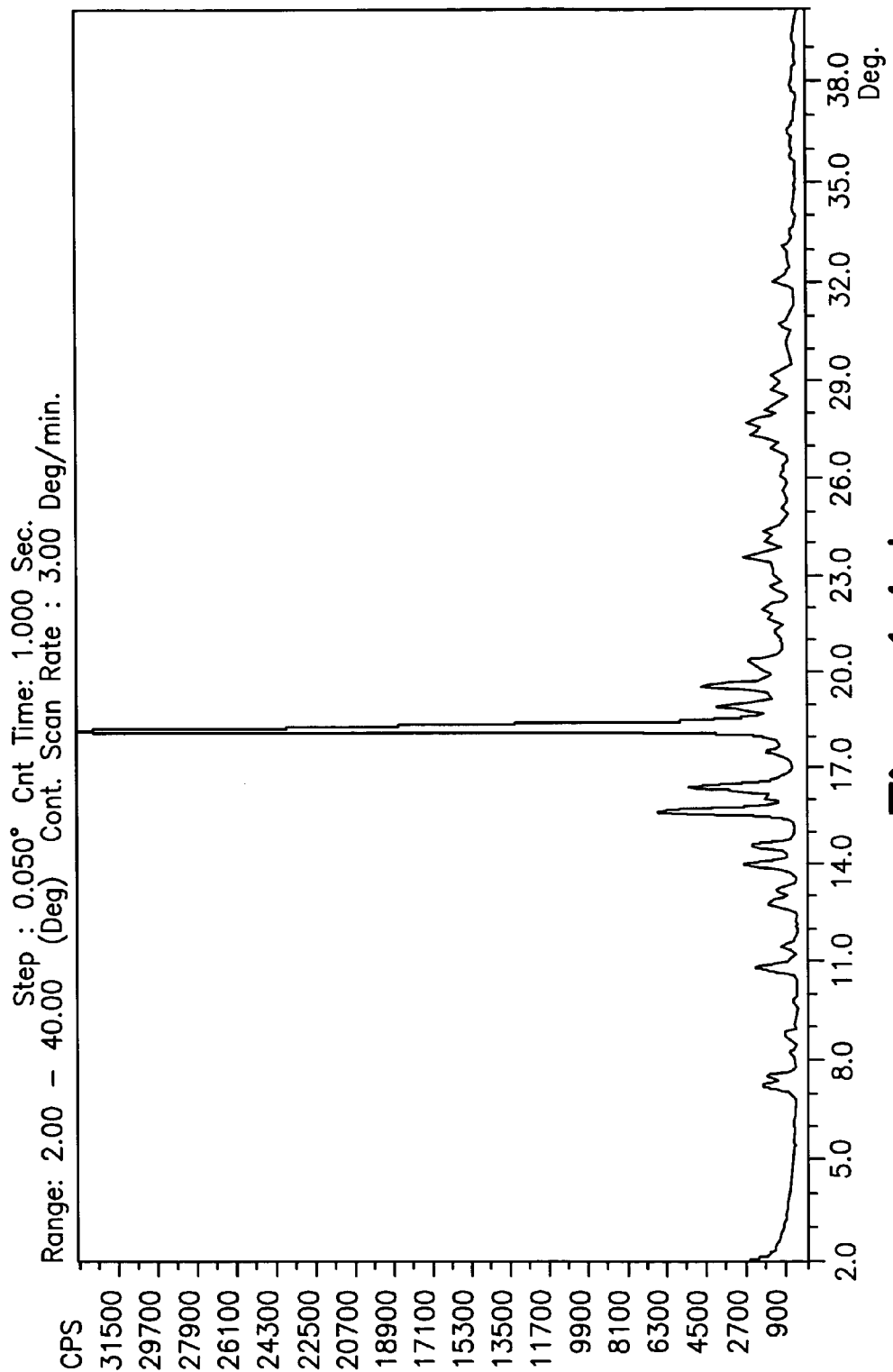
Figure 14F:
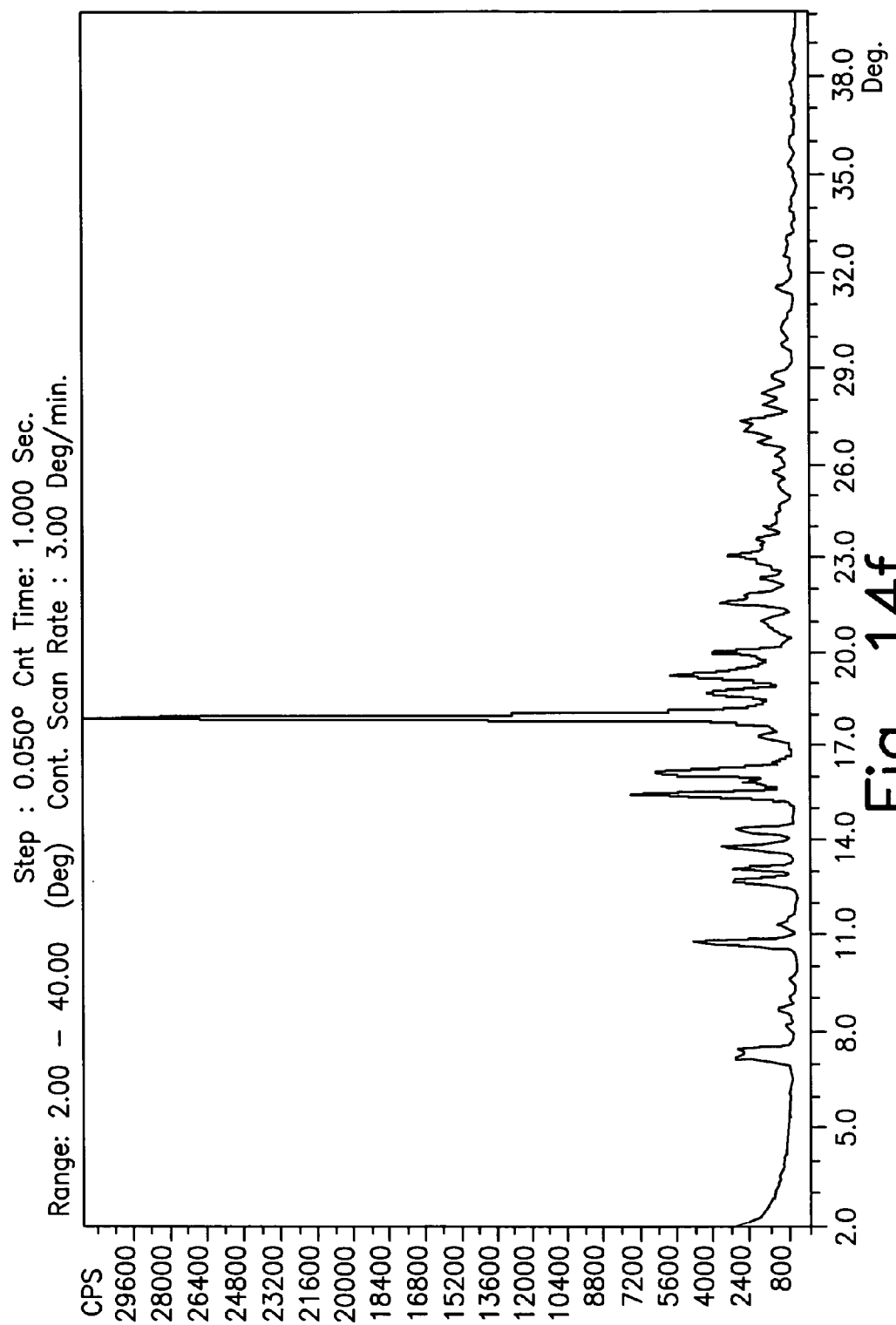
Figure 14G:
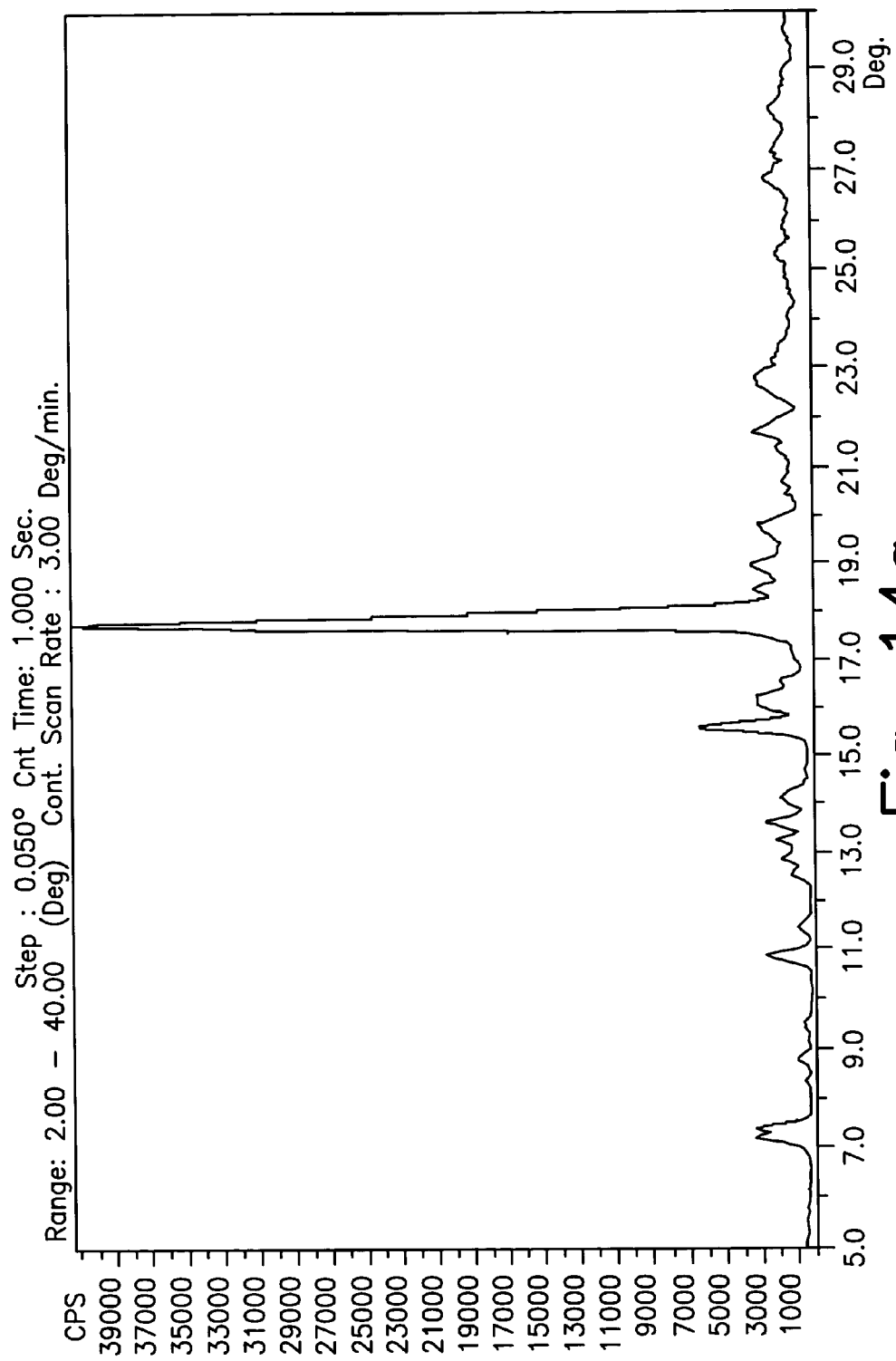

In another embodiment, the present invention provides a novel crystalline form of gatifloxacin, denominated form D, characterized by x-ray reflections at about 8.2°, 14.4°, 19.0°, 21.4°, 21.9°, and 23.1°±0.2° 2θ. A typical x-ray diffraction diagram for form D is shown in FIG. 11. A typical DSC thermogram of form D is shown in FIG. 12. Form D has a loss on drying of about 13 wt %. A typical TGA thermogram of form D is shown in FIG. 13.

Form D can be made by either a slurry process or a vapor incubation process. The slurry process for making form D includes the steps of slurrying gatifloxacin with methanol and isolating gatifloxacin form D. In the vapor incubation process, gatifloxacin is incubated in vapors of methanol.

In still a further embodiment, the present invention provides a novel crystalline form of gatifloxacin, denominated form E1. Form E1 can be characterized by x-ray reflections at about 7.1°, 7.3°, 10.8°, 15.7°, 16.4°, and 18.1°±0.2° 2θ. Typical x-ray diffraction diagrams for different batches of form E1 are shown in FIGS. 14a through 14g, which suggest that small changes in the x-ray pattern may be observed in different batches, especially in the range of 19° to 30° 2θ.

Form E1 contains up to about 10% acetonitrile, water, or mixtures thereof. Form E1-ACN containing 8% to 10% acetonitrile can be referred to as monosolvate. The crystallographic properties of E1 are essentially insensitive to the presence of the solvent. The solvent can be driven-off by heating.

Figure 16:
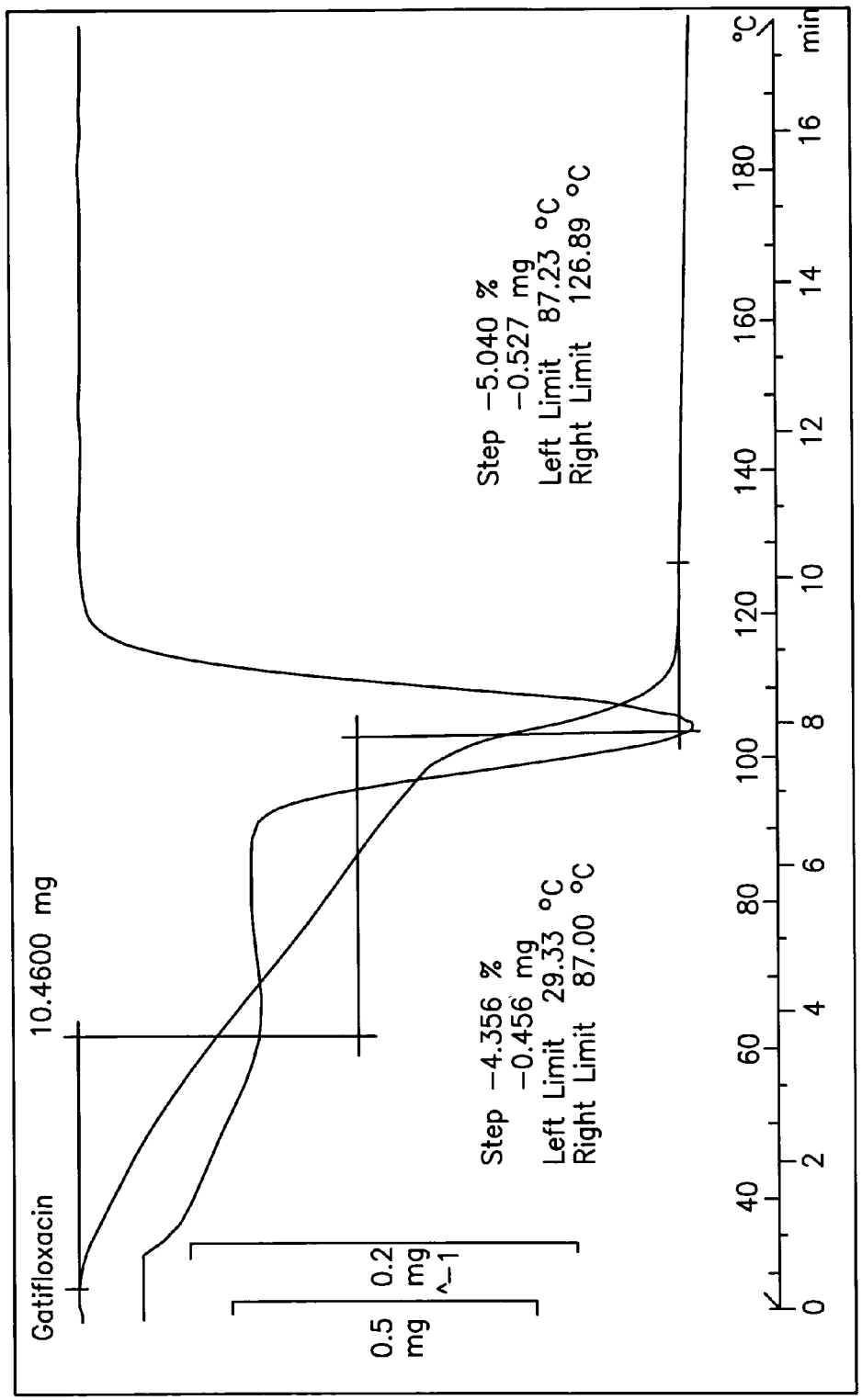
FIG. 16 shows a representative TGA thermogram of gatifloxacin form E1 as its acetonitrile solvate.

In a particular embodiment, the present invention provides a crystalline form of gatifloxacin, denominated E1-ACN, that has the crystallographic properties of E1 and contains up to about 10% acetonitrile. A typical TGA thermogram of E1-ACN is shown in FIG. 16. Drying of E1-ACN at 70° to 170° C. for at least about 30 minutes yields gatifloxacin form omega (Ω).

E1-ACN can be made by a crystallization process including the steps of providing, at reflux, a solution of gatifloxacin in acetonitrile, wherein the water content of the solution is about 5 wt % or less, preferably 4.5 wt % or less, cooling the solution to a seeding temperature between about 57° to 70° C., preferably about 60° C., seeding the solution with gatifloxacin, optionally maintaining the seeded solution at the seeding temperature for a seeding time of about 30 minutes or more, cooling the seeded solution to a temperature at which E1-ACN crystallizes, especially to ambient temperature or below, preferably about 5° C. or below, and isolating the gatifloxacin E1-ACN. Typically, E1-ACN is isolated from a suspension.

The water content of the solution prior to seeding should be about 5 wt % or less, preferably 4.5 wt % or less, as determined by Karl-Fisher analysis. If necessary, the water content can be reduced by distilling-off acetonitrile-water azeotrope (replenishing acetonitrile as required).

E1-ACN can also be made by a vapor incubation method in which gatifloxacin is incubated with vapors of acetonitrile for about 5 to about 20 days.

Figure 15:
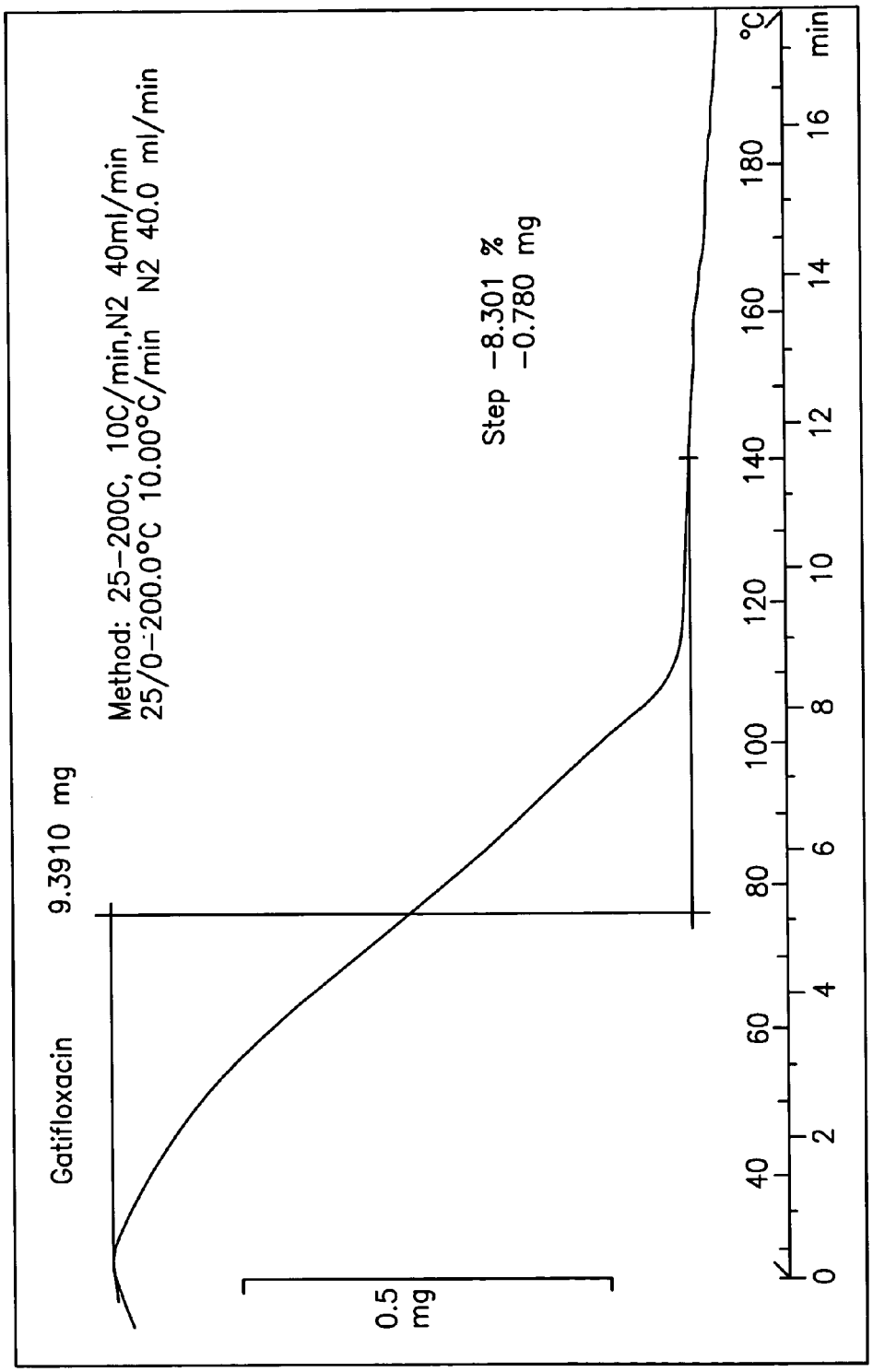
FIG. 15 shows a representative TGA thermogram of gatifloxacin form E1 dihydrate.

In another embodiment, the present invention provides a hydrate form of gatifloxacin having the crystallographic properties of form E1. The hydrated form can but preferably does not also contain acetonitrile, with the proviso that the total amount of water and acetonitrile is about 10% or less. In a preferred embodiment, the hydrated form contains about 7.5% to about 10% water and is a dihydrate. A typical TGA thermogram of form E1 dihydrate is shown in FIG. 15.

The crystallographic characteristics of hydrated form E1 are those of E1-ACN. Hydrated form E1 has a water content (Karl-Fisher) between about 5% and about 10%, preferably 7.5% to 10%. In a particular embodiment, the hydrated form of E1 is form E1 dihydrate and contains about 9% water.

Hydrated form E1 can be made in a treating process including the step of treating E1-ACN with a moist gas, such as air, nitrogen, or a noble gas. Preferably, the moisture content of the gas is such that the gas has a relative humidity between about 55% and 75%. The treating can be at any temperature from ambient up to about 60° C. Preferably, the treating is at about 20° to 30° C., most preferably 25° C.

Treating E1-ACN solvate with a moist gas at higher temperature than 30° C. results in hydrated E1 that can contain 5% to 7% water. By treating the E1 product which contains 5% to 7% water with a moist gas (55% -75% relative humidity) at 20° to 30° C., preferably 25° C., hydrated E1 (water content of 7.5% to 10%) is obtained. In preferred embodiments, E1 dihydrate of 9.3% water content is obtained.

Any apparatus that allows for circulation or percolation of moist gas around and between particles of the E1-ACN can be used. Fluidized bed apparatus, well known in the art, is particularly well suited for the treating.

The skilled artisan will know to adjust, within the limits discussed above, the time and temperature to achieve the desired water content. If the water content of a particular treated batch is lower than desired (or the acetonitrile content higher than desired), the batch can simply be treated further to achieve the desired levels of water and acetonitrile.

The hydrated E1, especially E1 dihydrate, obtained in this or any other embodiment of the present invention is substantially free of prior-art sesquihydrate. By substantially free is meant that the dihydrate contains about 5% or less of sesquihydrate.

A suitable method to determine the presence of gatifloxacin sesquihydrate in gatifloxacin form E1 is x-ray powder diffraction. Determination of presence of sesquihydrate in form E1 is feasible in the region 7° to 9° 2θ, where a peak of sesquihydrate appears at about 7.8° 2θ.

Moreover, the dihydrate of the present invention is stable against transformation to the sesquihydrate when exposed at ambient temperature to 60% relative humidity for one week. A sample is considered stable if the sesquihydrate content does not rise by an amount detectable by PXRD, described above, upon storage.

The E1 dihydrate of the present invention is stable against transformation to sesquihydrate when stored at 30° C. and 60% relative humidity for 3 months.

Figure 17:
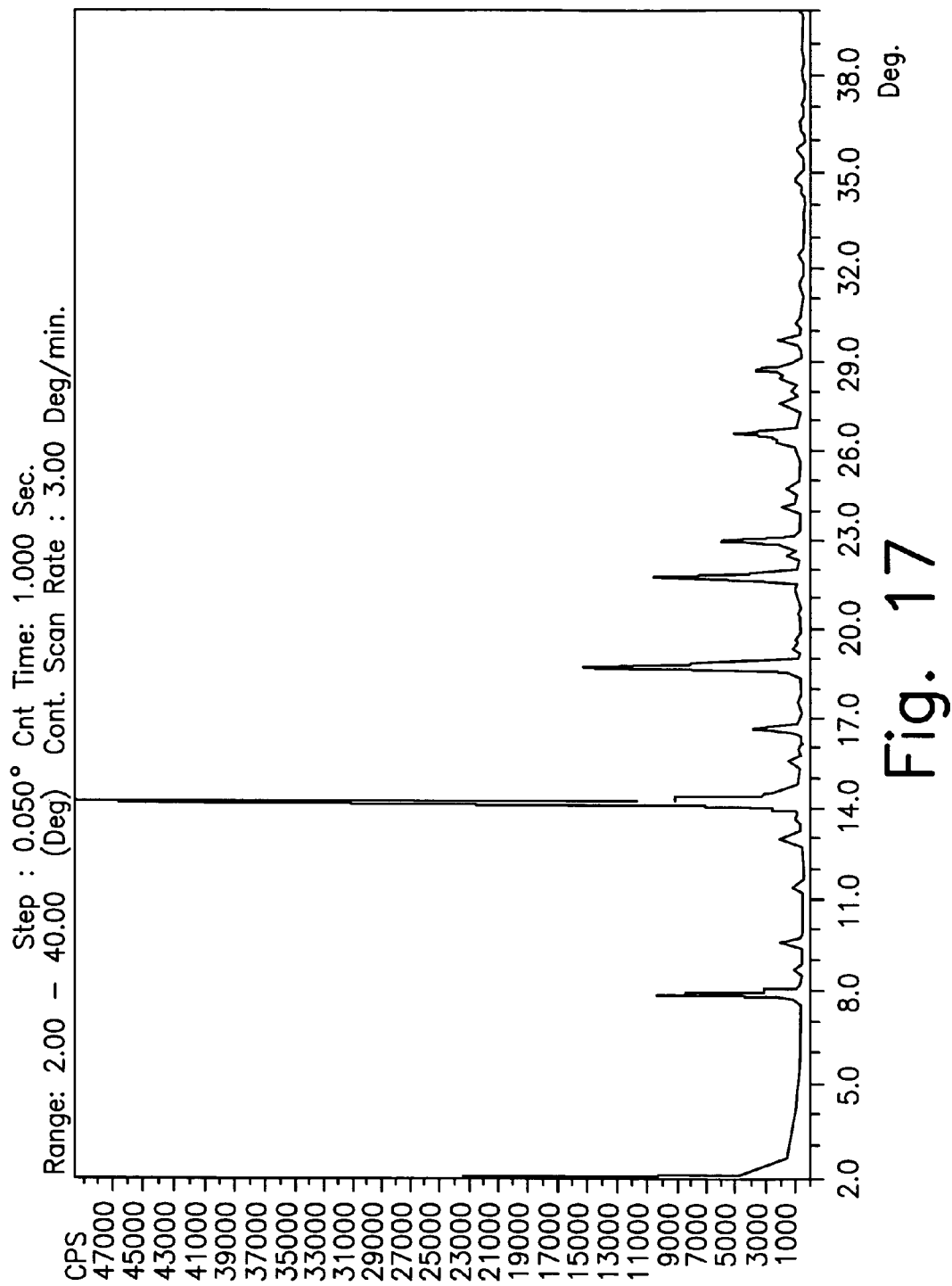
FIG. 17 shows a representative x-ray diffraction diagram of gatifloxacin form F.
Figure 18:
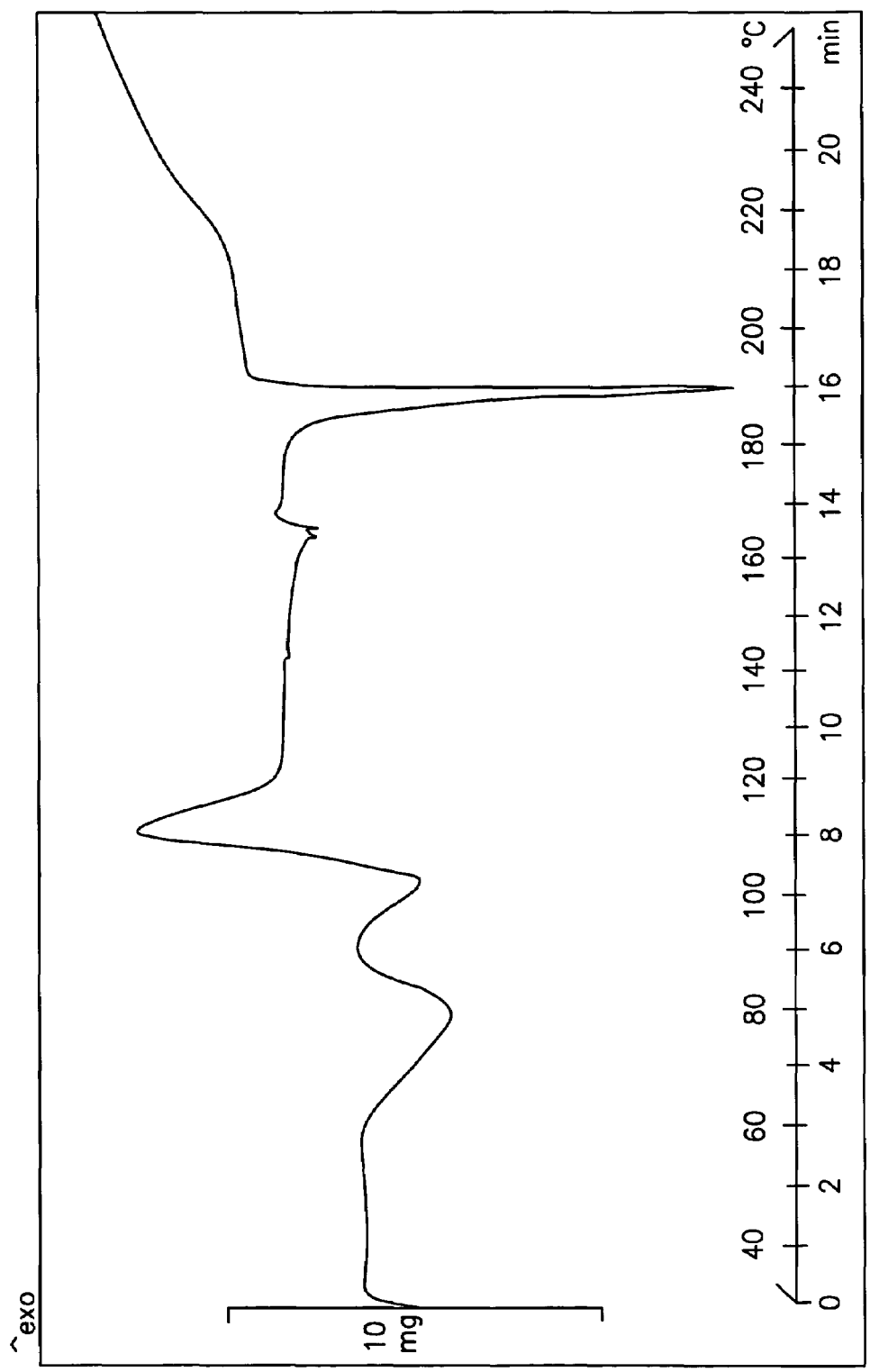
FIG. 18 shows a representative DSC thermogram of form F.
Figure 19:
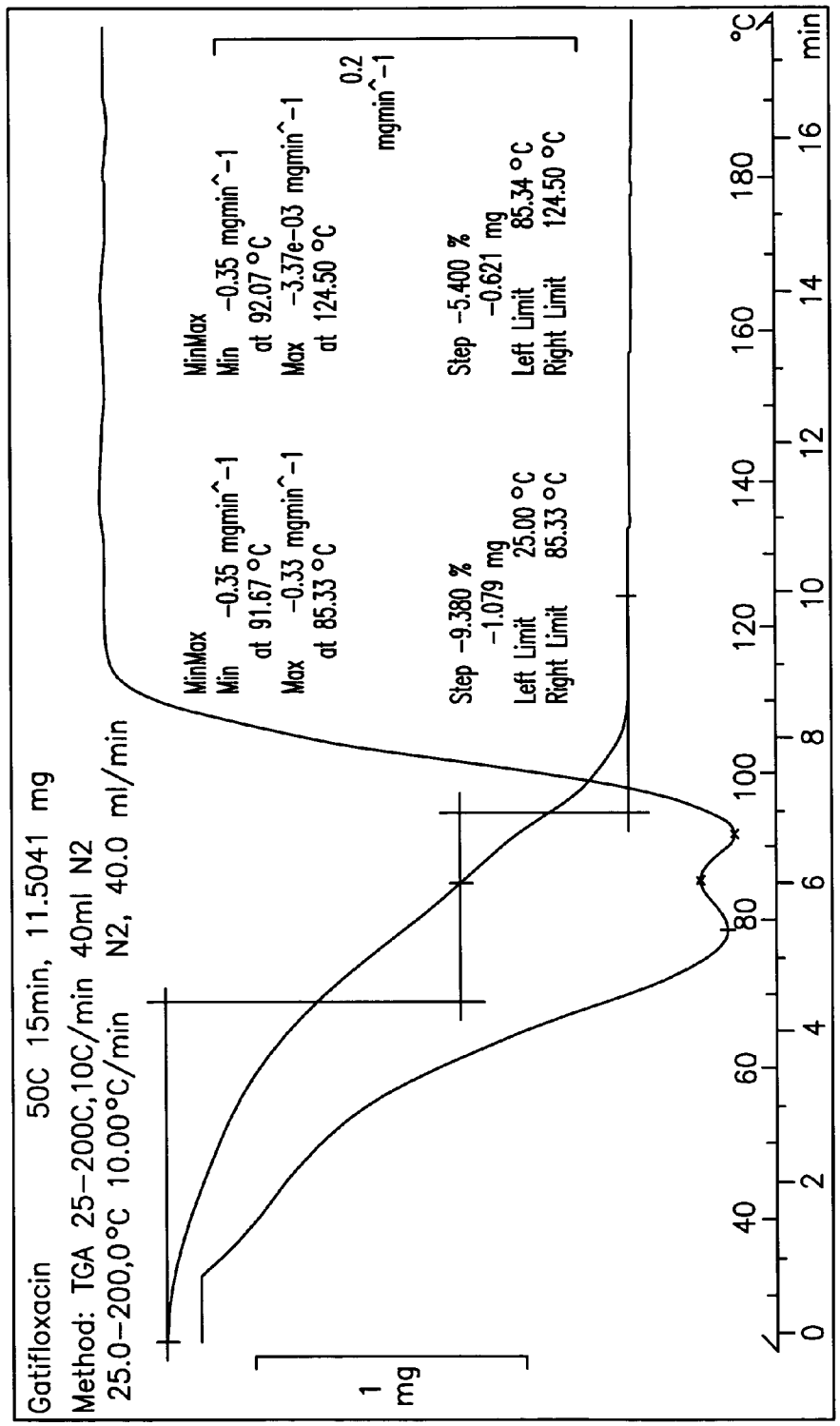
FIG. 19 shows a representative TGA thermogram of form F.

In another embodiment, the present invention provides a novel crystalline form of gatifloxacin, denominated form F, characterized by x-ray reflections at 8.0°, 14.2°, 18.7°, 21.8°, and 23.0°±0.2° θ. A typical x-ray diffraction diagram of form F is shown in FIG. 17. A typical DSC thermogram of form F is shown in FIG. 18. A typical TGA thermogram of form F is shown in FIG. 19.

Form F can be made by a crystallization method including the steps of providing a solution, about 25% solids, of gatifloxacin in a mixture of methanol and water, 90:10 (v:v); cooling the solution, especially to ambient temperature or below; and isolating the crystalline form of gatifloxacin from the suspension. Drying form F yields form G, described herein below.

In still a further embodiment, the present invention provides a novel crystalline form of gatifloxacin, denominated form G, characterized by at least one of:

a) x-ray reflections at about 17.2° and 17.6°±0.2° 2θ, or b) FTIR absorption bands at about 1614 cm$^{-1}$ and about 1267 cm$^{-1}$.

Figure 20:
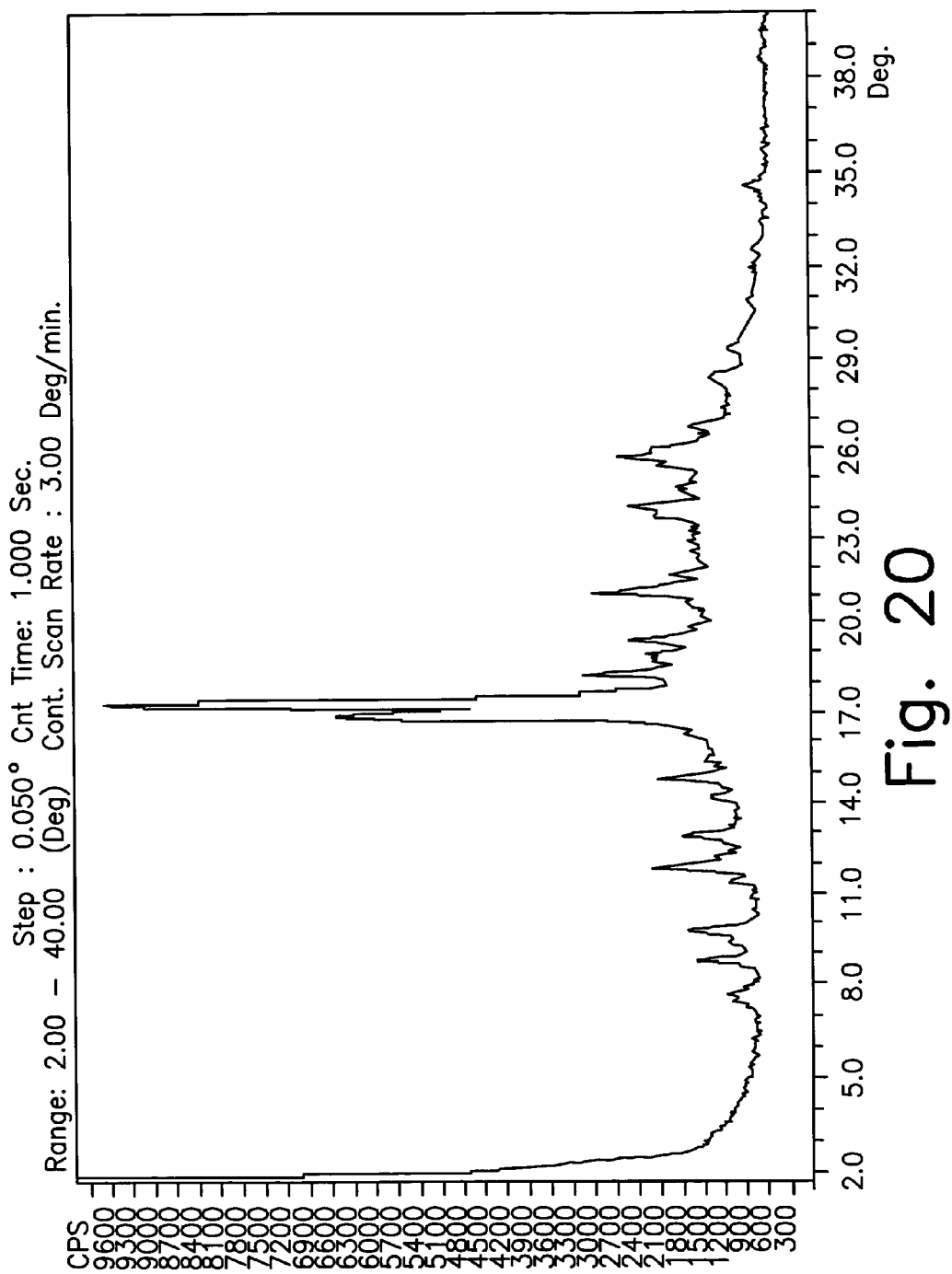
FIG. 20 shows a representative x-ray diffraction diagram of gatifloxacin form G.
Figure 21:
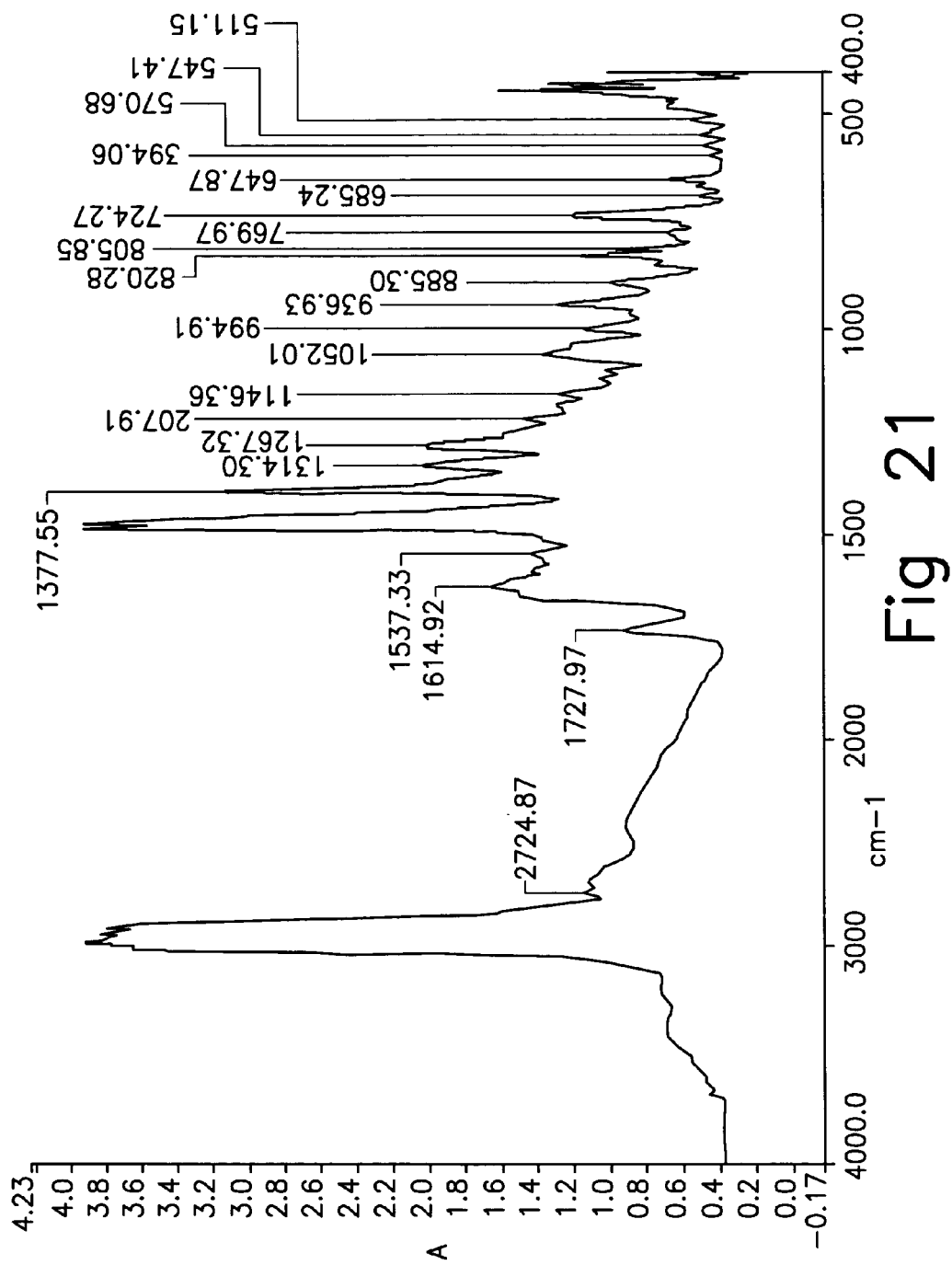
FIG. 21 shows a representative FTIR spectrum of gatifloxacin form G.
Figure 22:
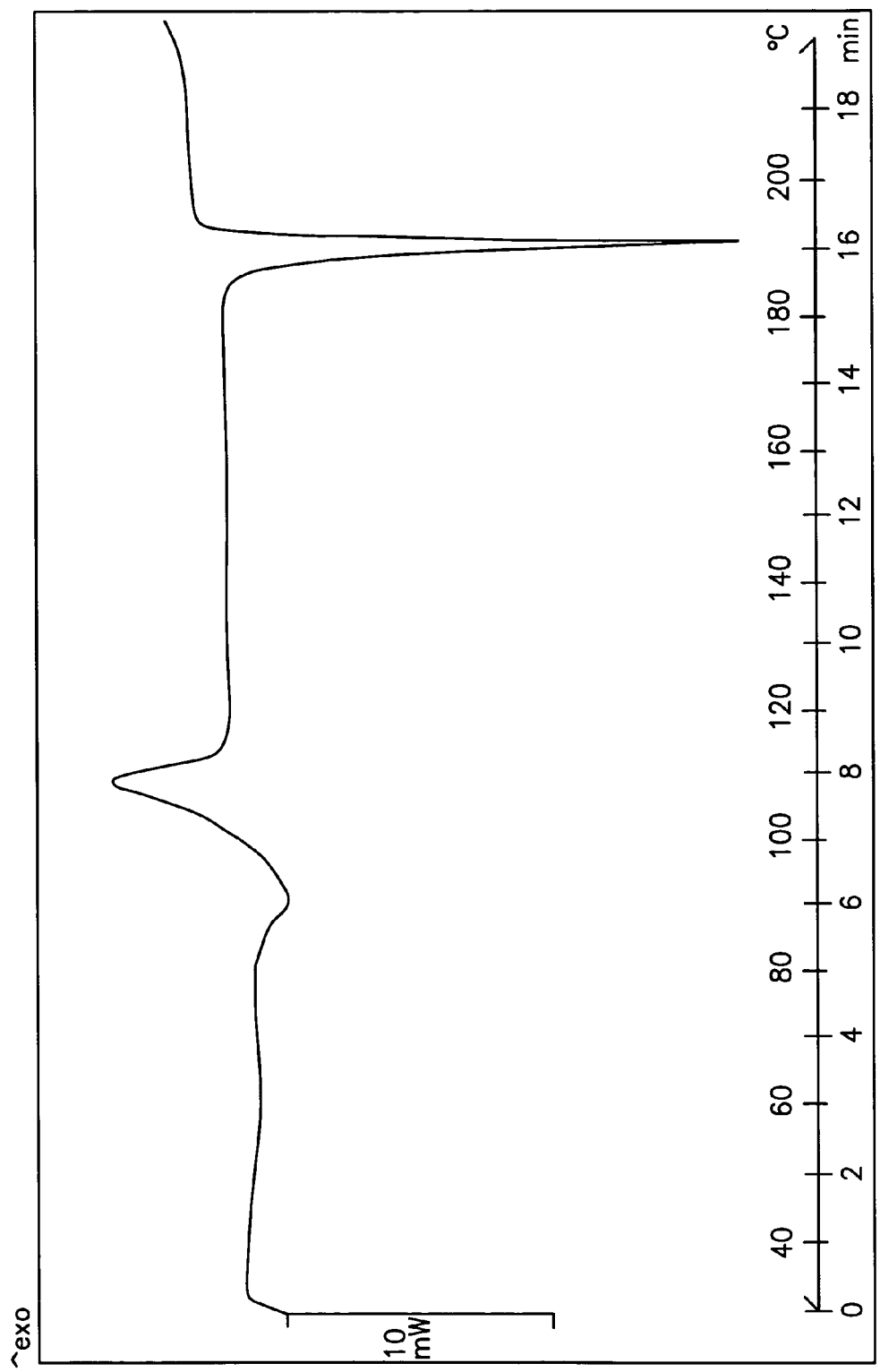
FIG. 22 shows a representative DSC thermogram of gatifloxacin form G.
Figure 23:
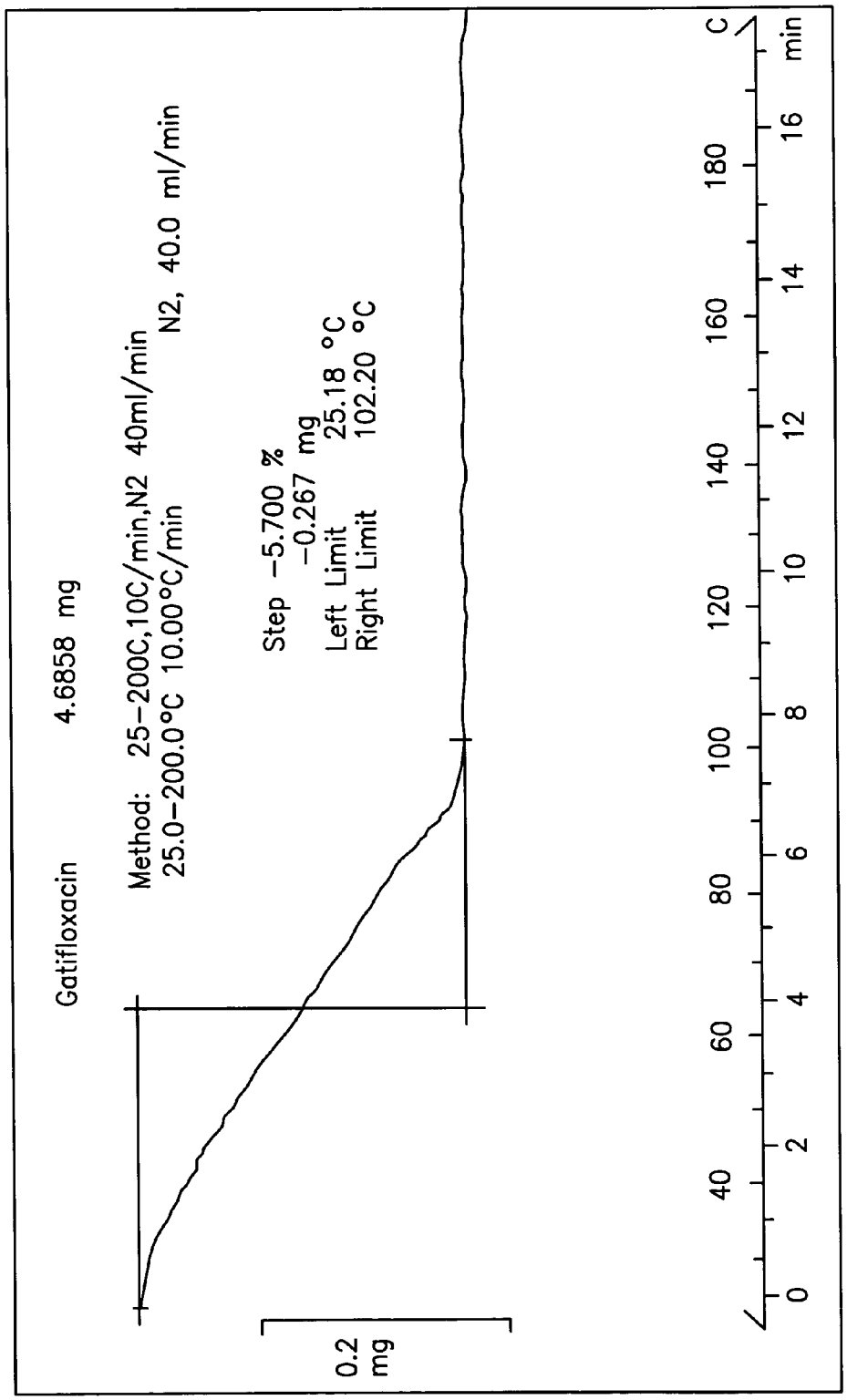
FIG. 23 shows a representative TGA thermogram of gatifloxacin form G.

A typical x-ray diffraction diagram of form G is shown in FIG. 20. A typical FTIR spectrum of form G is shown in FIG. 21. A typical DSC thermogram of form G is shown in FIG. 22. A typical TGA thermogram of form G is shown in FIG. 23.

Form G can be made by, for example, drying either of form A or form F at about 50° C. and atmospheric pressure for at least about 20 hours.

Figure 24:
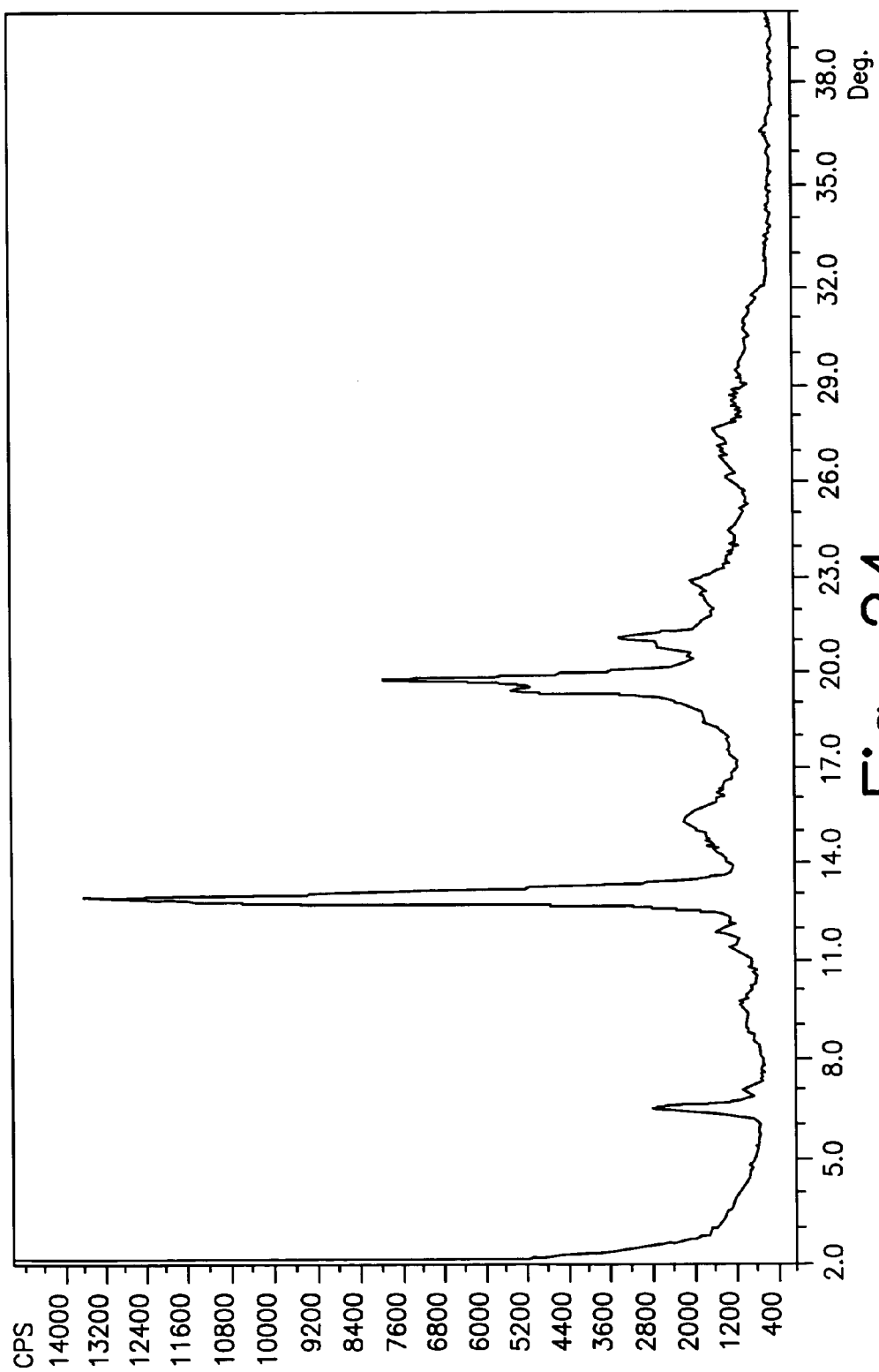
FIG. 24 shows a representative x-ray diffraction diagram of gatifloxacin form H toluene solvate.
Figure 25:
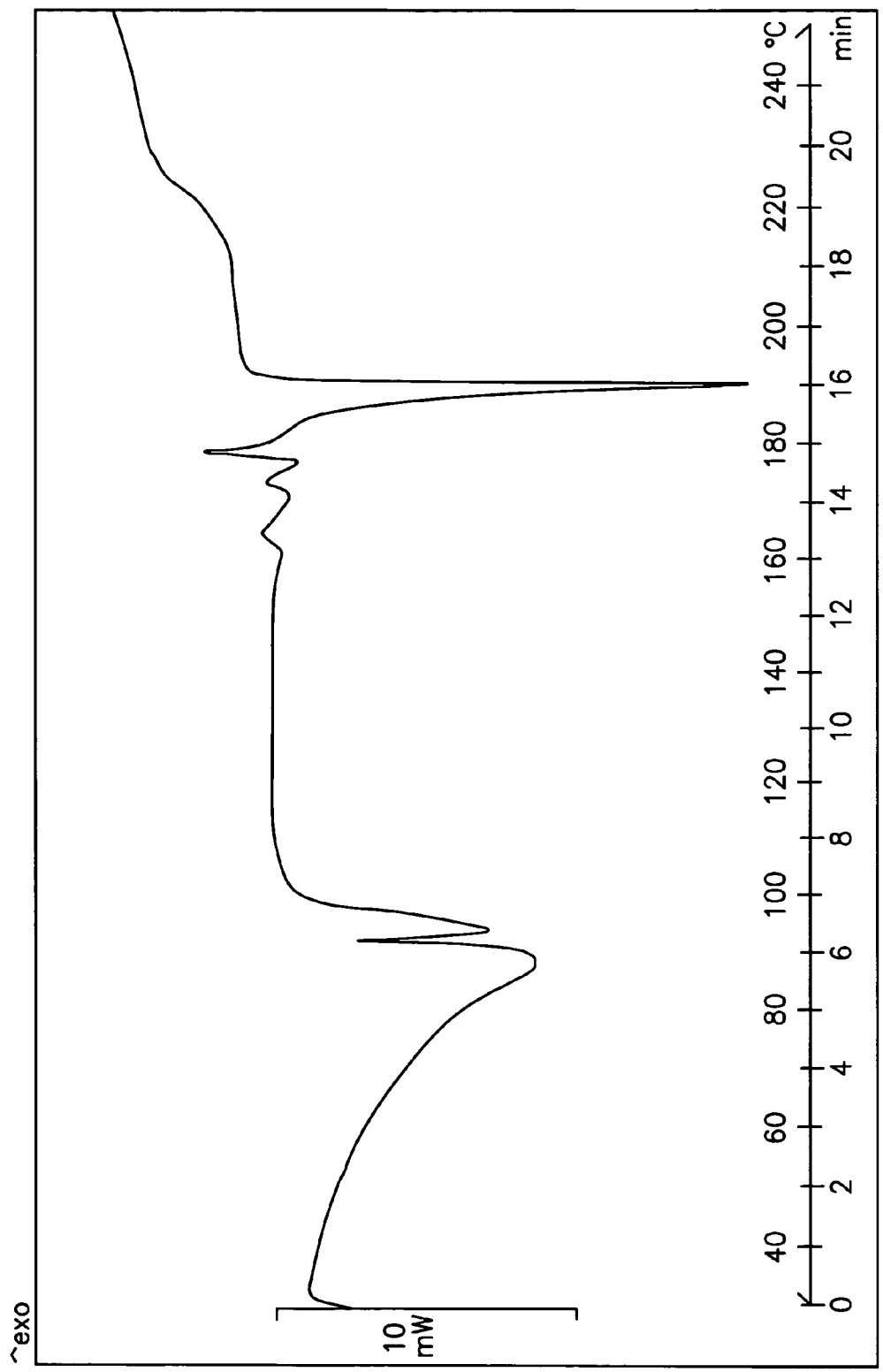
FIG. 25 shows a representative DSC thermogram of gatifloxacin form H toluene solvate.
Figure 26:
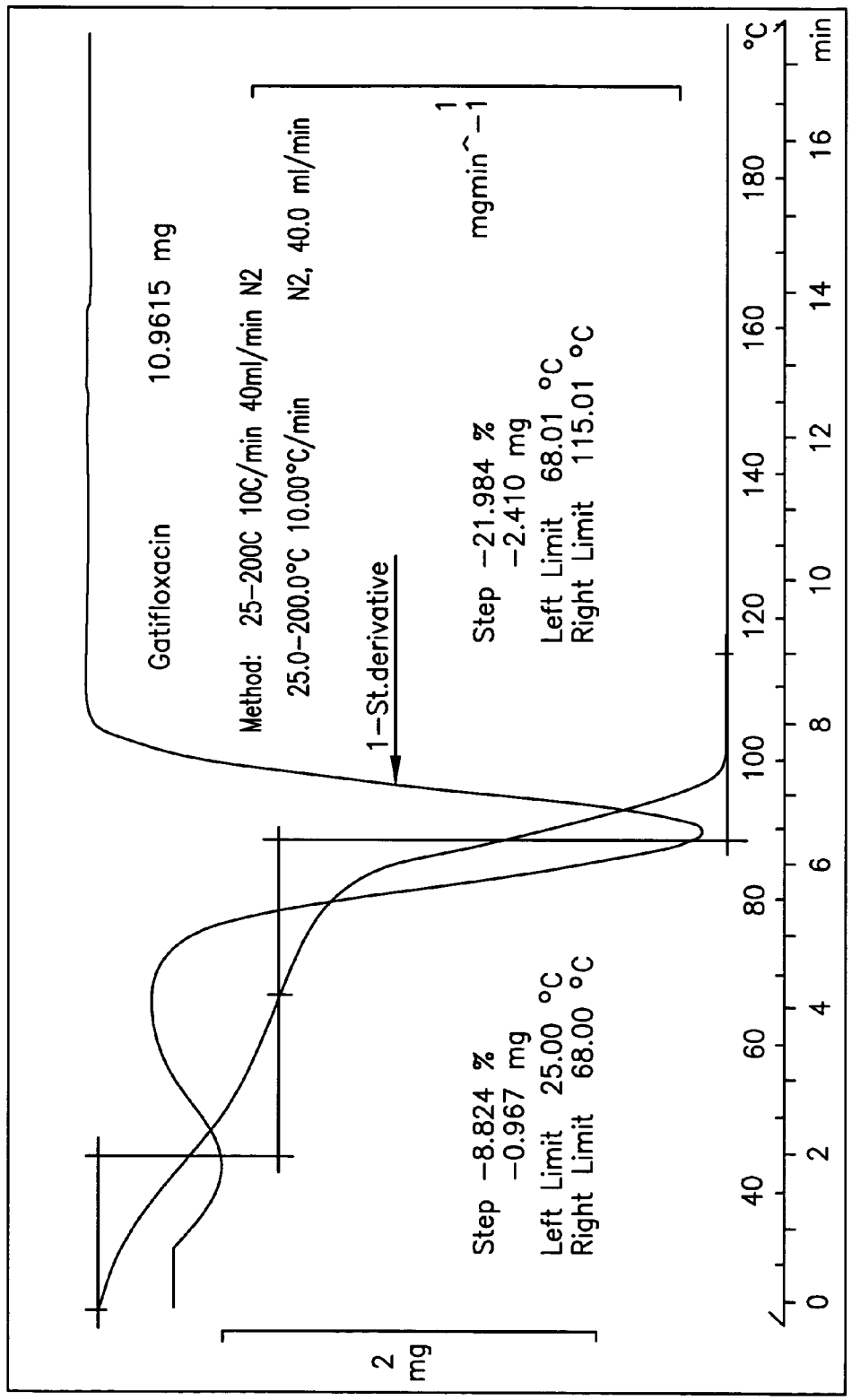
FIG. 26 shows a representative TGA thermogram of gatifloxacin form H toluene solvate.

In a further embodiment, the present invention provides a novel crystalline form of gatifloxacin, denomonated form H. Form H is characterized by x-ray reflections at about 6.6°, 13.2°, 19.6°, and 19.9°±0.2°2θ. A typical x-ray diffraction diagram of form H toluene solvate is shown in FIG. 24. A typical DSC thermogram of form H toluene solvate is shown in FIG. 25. A typical TGA thermogram of form H toluene solvate is shown in FIG. 26.

Form H can be made by a crystallization method including the steps of: providing a solution of gatifloxacin in toluene, preferably at reflux; cooling the solution to a temperature at which form H crystallizes, especially to ambient temperature or below, preferably 5° C. or below, and isolating the crystalline form of gatifloxacin from the suspension.

Form H can also be prepared by a slurry method including the steps of slurrying gatifloxacin in toluene at ambient temperature for a slurry time and isolating the crystalline form of gatifloxacin from the slurry. Preferred slurry times are between about 8 and about 36 hours.

Figure 27:
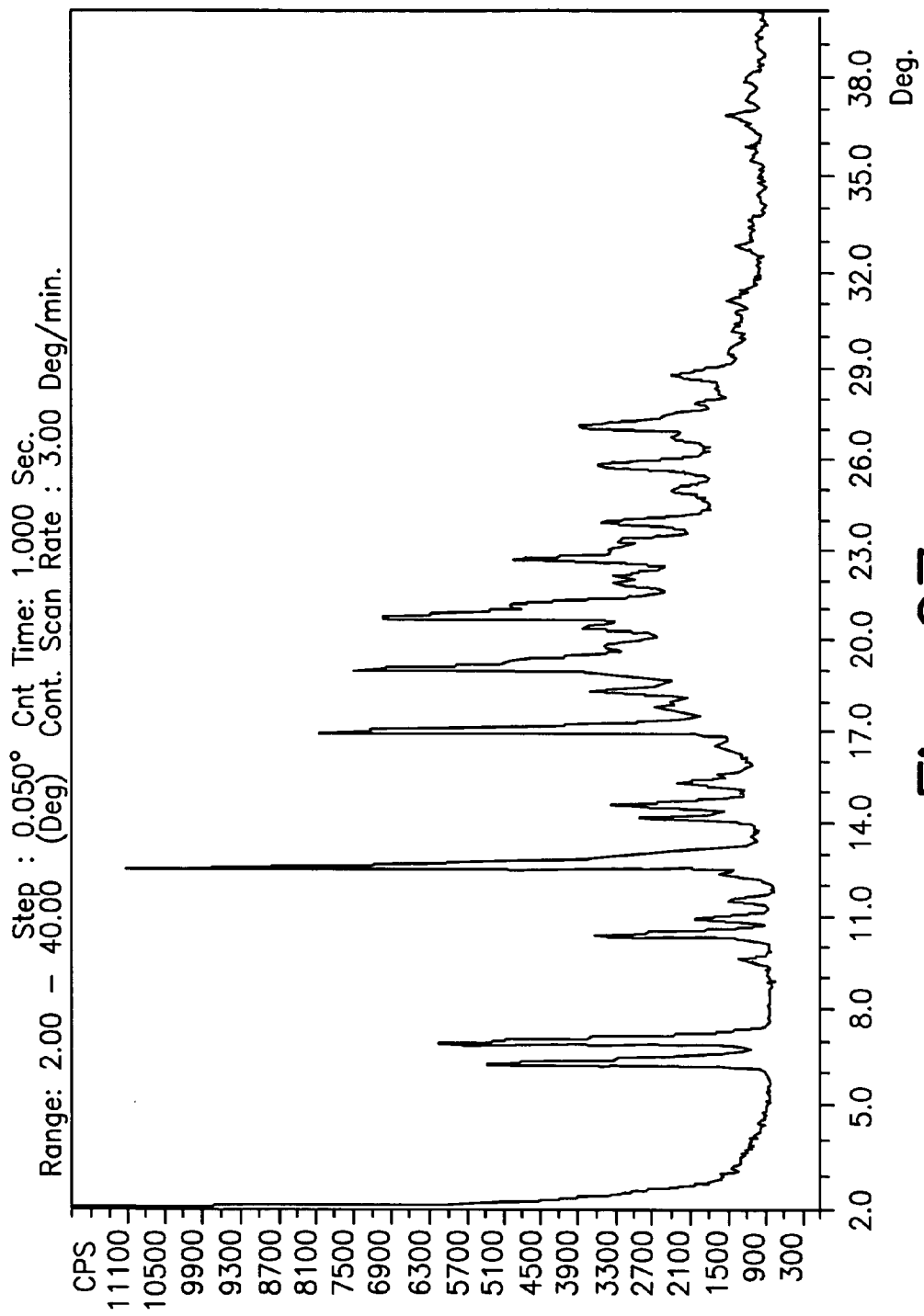
FIG. 27 shows a representative x-ray diffraction diagram of gatifloxacin form I.
Figure 28:
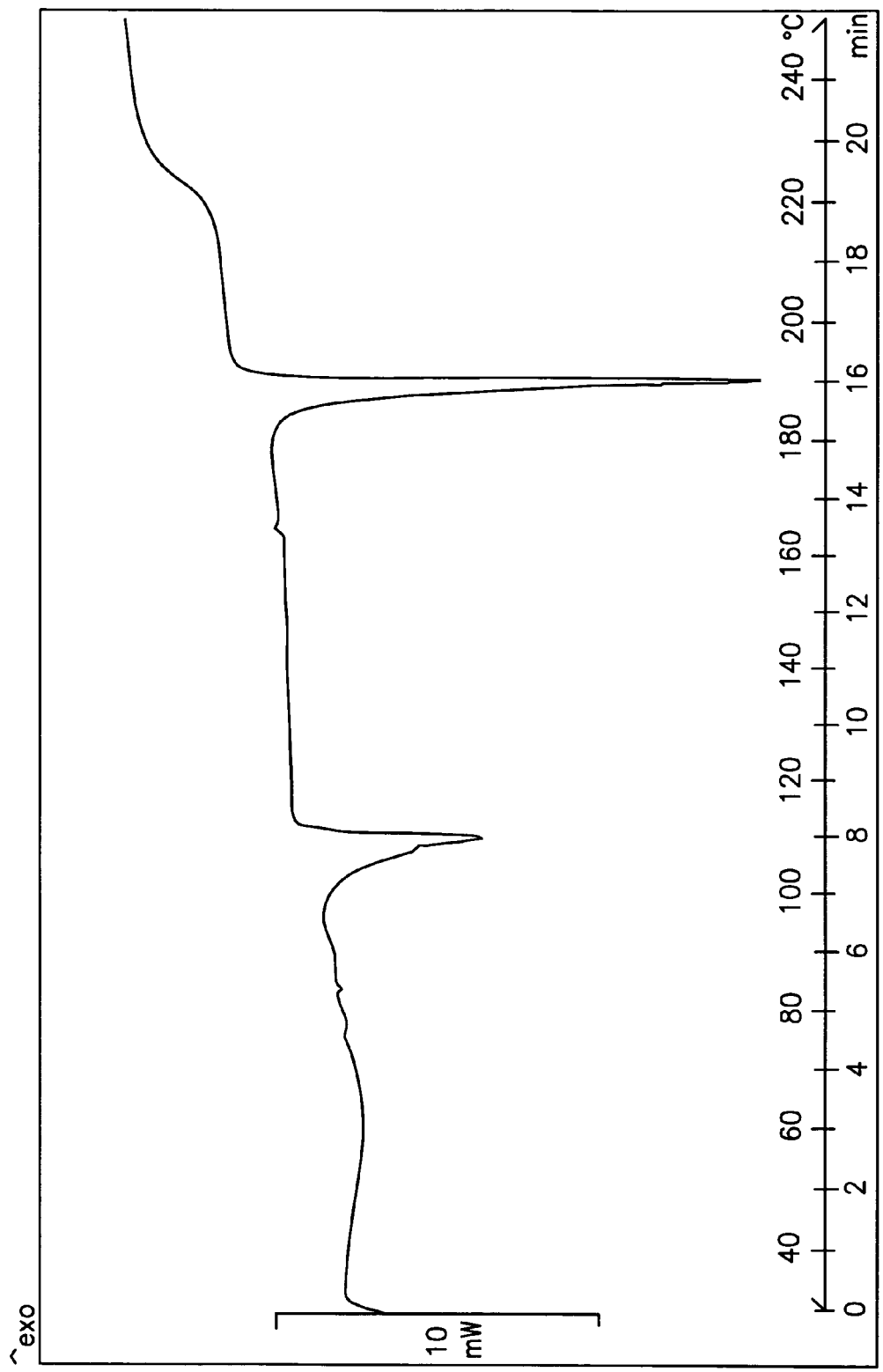
FIG. 28 shows a representative DSC thermogram of gatifloxacin form I.
Figure 29:
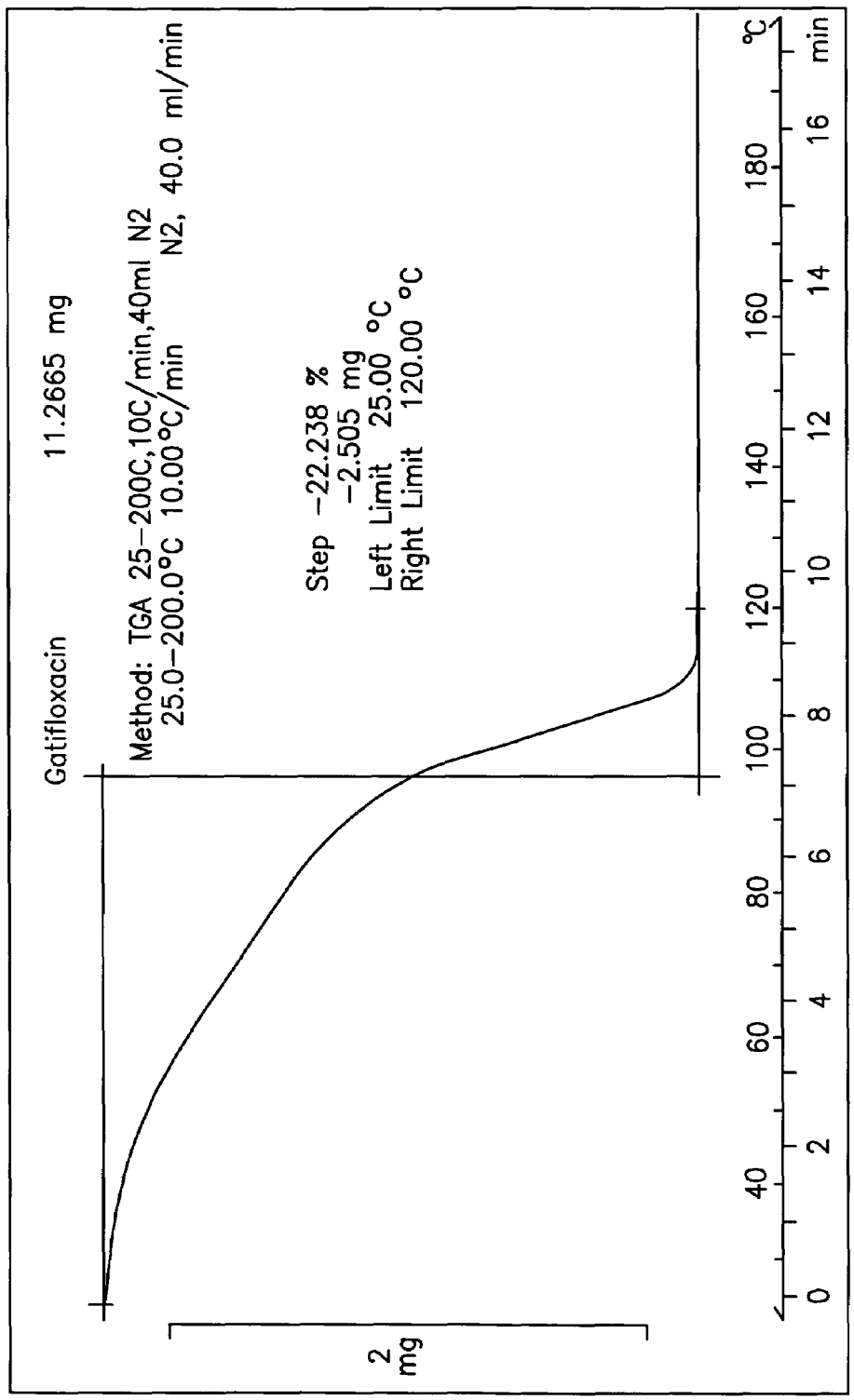
FIG. 29 shows a representative TGA thermogram of gatifloxacin form I.

In a further embodiment, the present invention provides a novel crystalline form of gatifloxacin, denominated form I and characterized by x-ray reflections at 6.5°, 7.1°, 12.8°, 17.2°, 19.3°, and 21.0°±0.2°. A typical x-ray diffraction diagram of form I is shown in FIG. 27. A typical DSC thermogram of form I is shown in FIG. 28. A typical TGA thermogram of form I is shown in FIG. 29.

Form I can be made by a crystallization method including the steps of:

a) providing a solution of gatifloxacin in 1-butanol, b) cooling the solution to a temperature at which form I crystallizes, especially to ambient temperature or below to obtain a suspension, and c) isolating the crystalline form of gatifloxacin from the suspension.

Form I converts to hereinbelow described form J upon drying.

Figure 30:
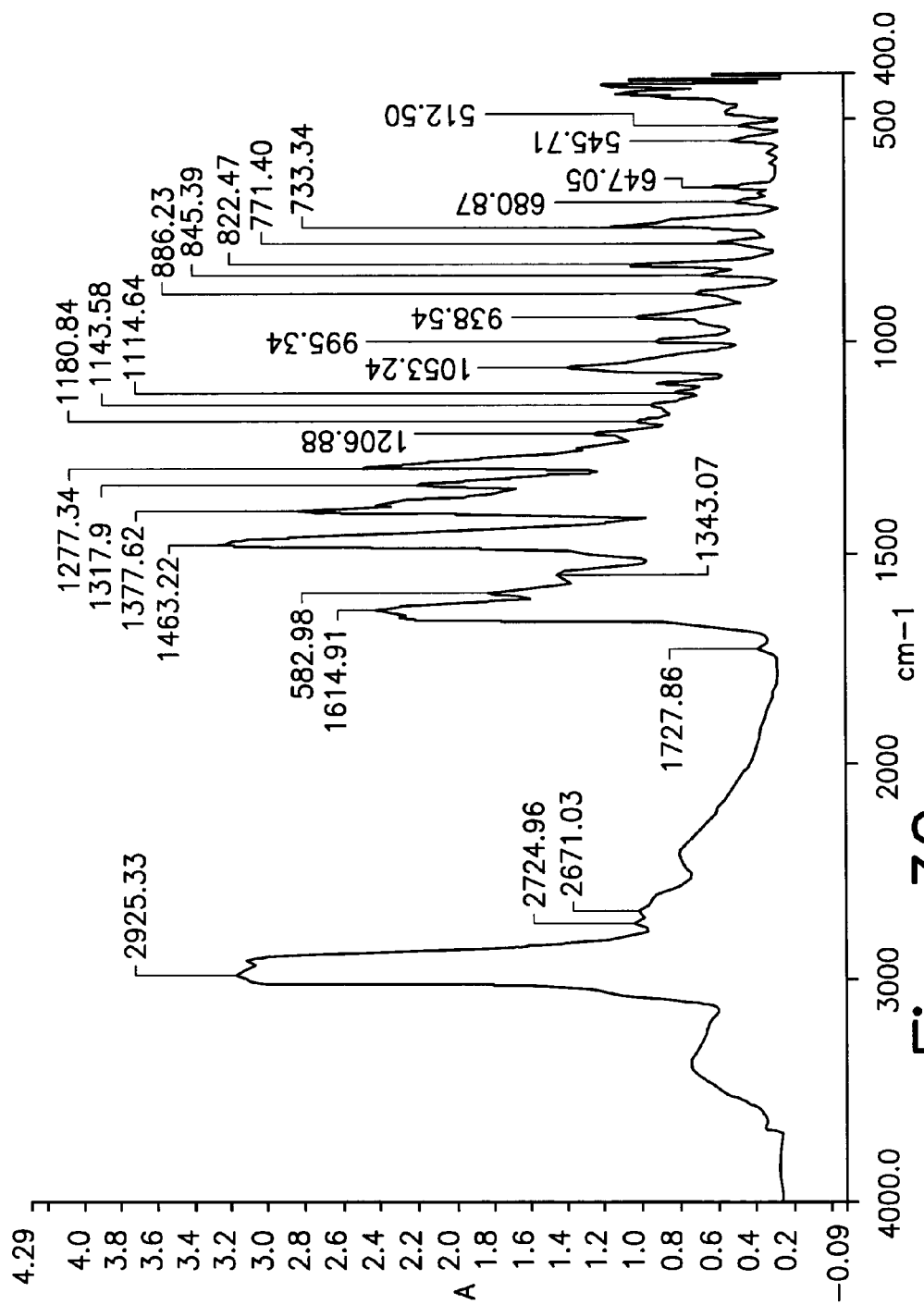
FIG. 30 shows a representative FTIR spectrum of gatifloxacin form J.
Figure 31:
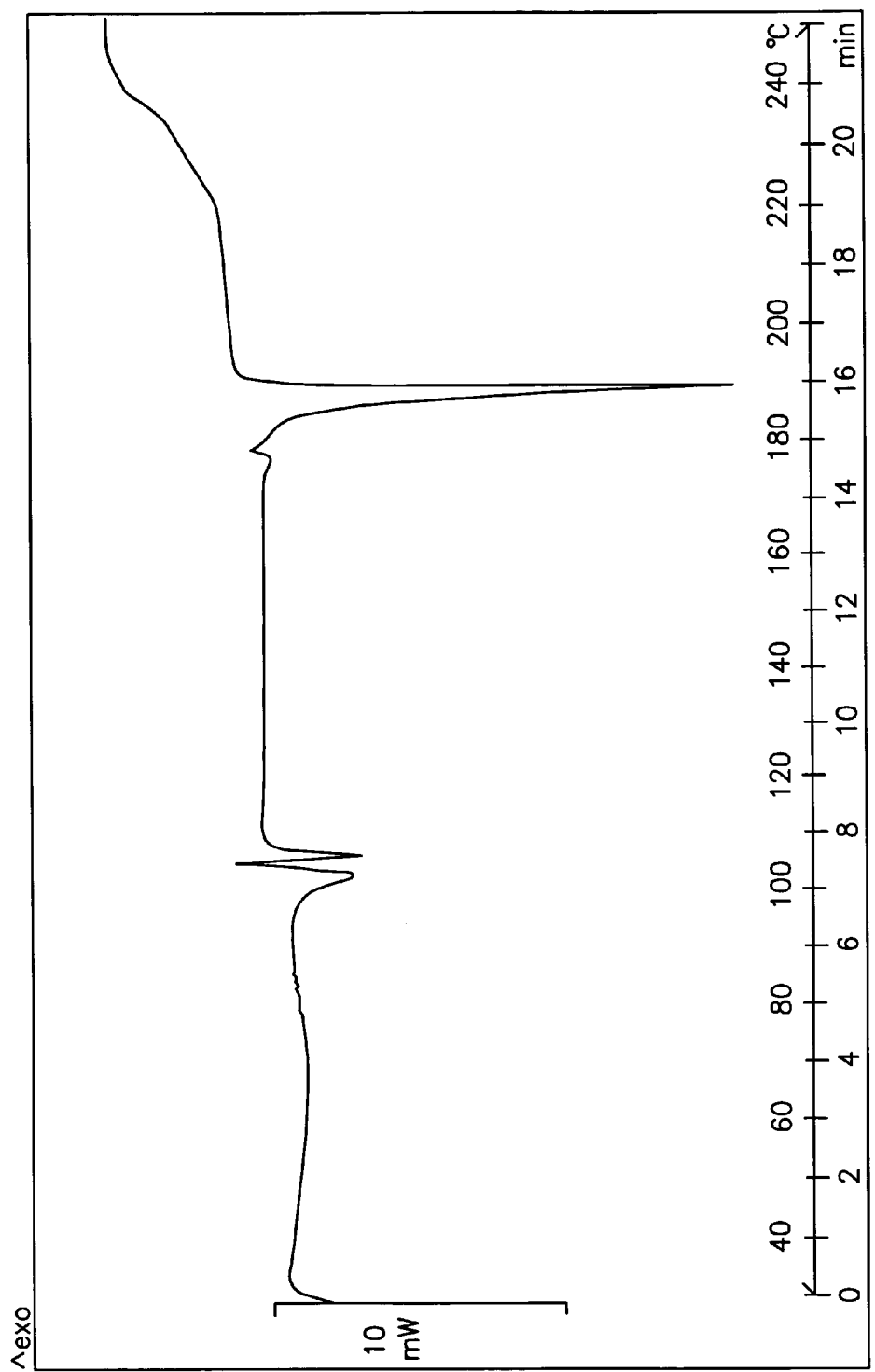
FIG. 31 shows a representative DSC thermogram of gatifloxacin form J.
Figure 32:
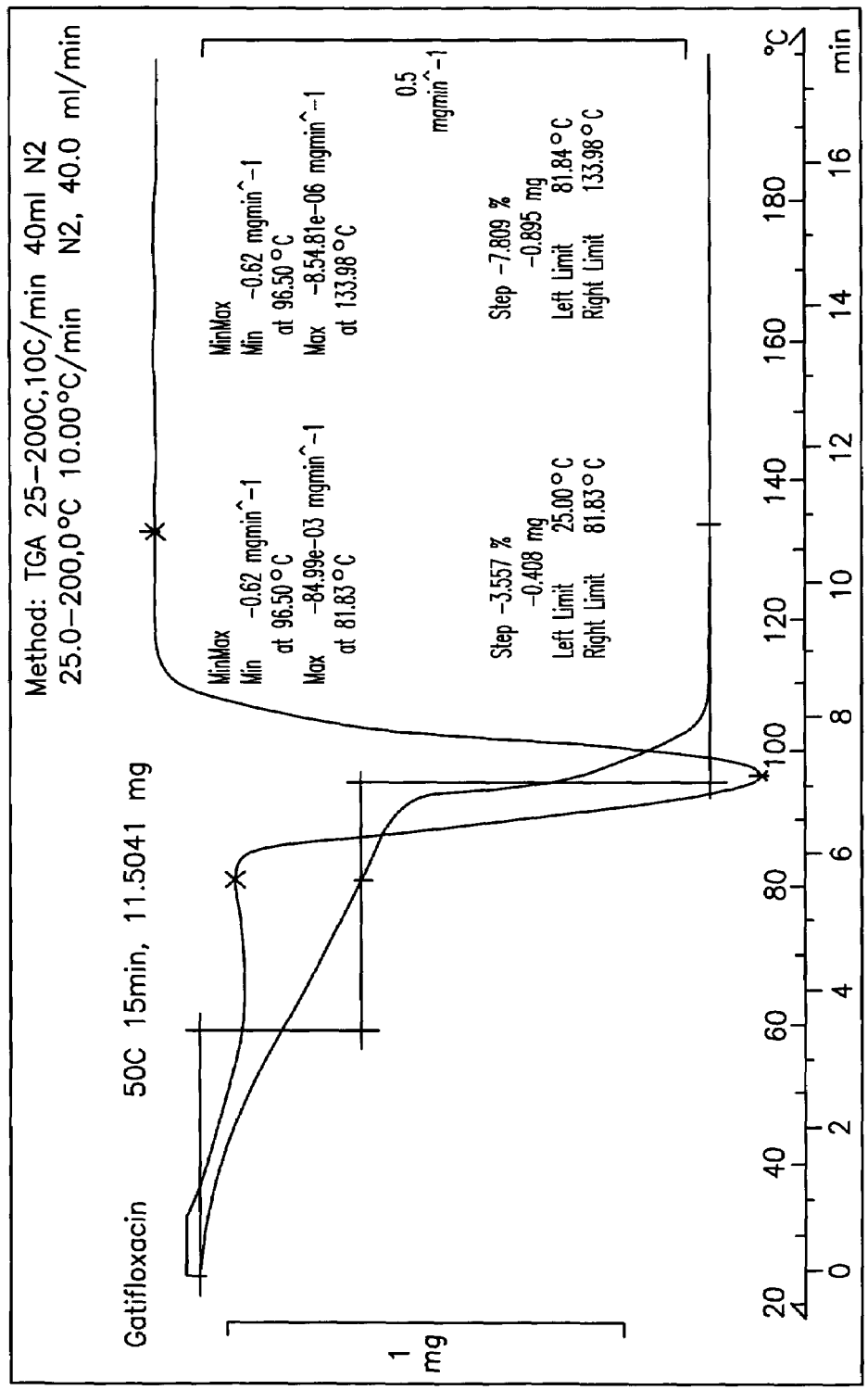
FIG. 32 shows a representative TGA thermogram of gatifloxacin form J.

In still another embodiment, the present invention provides a novel crystalline form of gatifloxacin, denominated form J, that exists as multiple solvates. Regardless of solvation, form J is characterized by x-ray reflections at about 6.7°, 11.3°, 13.8°, and 16.4°±0.2° 2θ. A typical FTIR spectrum of form J is shown in FIG. 30. A typical DSC thermogram of form J is shown in FIG. 31. A typical TGA thermogram of form J is shown in FIG. 32.

Form J as its iso-propanol solvate can be made by incubating gatifloxacin in vapors of iso-propanol, or by a crystallization method that includes the steps of:

a) providing a solution of gatifloxacin in iso-propanol, b) cooling the solution to a temperature at which form J crystallizes, especially ambient temperature or below, and c) isolating the crystalline form of gatifloxacin.

Form J as its iso-propanol solvate can also be made by heating gatifloxacin form A at about 40° to about 70° C., preferably about 50° C., and atmospheric pressure.

Form J as its methyl ethyl ketone solvate can be made by incubating gatifloxacin in vapors of methyl ethyl ketone.

Form J as its acetone solvate can be made by a slurry process including the steps of slurrying gatifloxacin in acetone at ambient temperature, and isolating the crystalline acetone solvate form J gatifloxacin from the slurry.

Form J as its tetrahydrofuran solvate can be made by a slurry process including the steps of slurrying gatifloxacin in tetrahydrofuran at ambient temperature, and isolating the crystalline form J tetrahydrofuran solvate.

Form J as its 1-butanol solvate can be made by a crystallization method including the steps of:
  a) providing a solution of gatifloxacin in 1-butanol, preferably at reflux
  b) cooling the solution to a temperature at which form J crystallizes, especially ambient temperature or below, especially about 5° C., and
  c) isolating the crystalline gatifloxacin form J 1-butanol solvate.

Total loss-on-drying (LOD) values, step weight-losses, and water contents for form J as several of its solvates are summarized in Table I below.

TABLE I

LOD, KF and Corresponding Solvate Formulas of form J Samples

| Solvent | Total Weight Loss By TGA (%) | Weight loss step (≈80-145° C.) | Karl Fisher (wt-%) | Corresponding Solvate Formula |
| --- | --- | --- | --- | --- |
| IPA | 8.7 | 4.1 | 4.01 | GTF:IPA (4:1) (Theoretical value: 3.8%) |
| 1-BuOH | 10.4 | 7.6 | 2.79 | GTF:n-BuOH (5:2) (Theoretical value: 7.3%) |
| IPA. | 8.7 | 6.4 | 2.42 | GTF:IPA (5:2) (Theoretical value: 6.0%) |
| IPA | 8.3 | 4.9 | 4.84 | GTF:IPA (3:1) (Theoretical value: 5.0%) |
| Acetone | 8.9 | 4.3 | 3.45 | GTF:Acetone (3:1) (Theoretical value: 4.9%) |
| IPA | 11.4 | 7.8 | 3.13 | GTF:IPA (2:1) (Theoretical value: 7.4%) |

In still further embodiments, the present invention provides methods of making the prior-art crystalline form of gatifloxacin denominated form omega (i).

In one such embodiment, the present invention provides a crystallization method of making gatifloxacin form omega including the steps of:
  a) providing a filtered solution of gatifloxacin in acetonitrile, wherein the solution has a water content of about 5% or less, preferably about 4.5 wt % or less, at a temperature of about 80° C. or higher, preferably
  b) cooling the solution to a seeding temperature of about 50° to about 56° C.
  c) seeding the solution with gatifloxacin at the seeding temperature and, optionally, maintaining the seeded solution at the seeding temperature for a seeding time of about 30 minutes or more,
  d) cooling the seeded solution to a temperature at which form omega crystallizes, preferably to ambient temperature or below, most preferably about 5° C., and
  e) isolating the gatifloxacin crystalline form omega.

As discussed in relation to for E1, the water content of the hot-filtered solution can be adjusted to the desired range by distilling off water-acetonitrile azeotrope.

In another embodiment, the present invention provides a method of making gatifloxacin form omega including the step of heating form J to about 90° to about 170° C., preferably about 120° C., at atmospheric pressure.

In a further embodiment, the present invention provides a method of making gatifloxacin form omega including the steps of heating form E1 at about 70° to 170° C. for at least about 30 minutes.

In yet still a further embodiment, the present invention provides a method of making gatifloxacin form omega including the steps of heating gatifloxacin form G at about 120° C. In yet other embodiments, the present invention provides a method of making the prior art hemihydrate crystalline form of gatifloxacin, denominated T2RP, via the novel gatifloxacin E1. Thus in one embodiment, useful when the amounts of gatifloxacin are about 200 g or less, the present invention provides a method of making T2RP including the steps of slurrying gatifloxacin E1 with ethanol, isolating the solid from the slurry, and drying the solid in vacuo to obtain gatifloxacin T2RP.

In a related embodiment, useful with >200 gram quantities of gatifloxacin or more, the present invention provides a method of making gatifloxacin form T2RP including the steps of slurrying kilogram quantities of gatifloxacin in ethanol isolating the solid from the slurry, and treating the isolated solid with moist air, as is done in making E1 dihydrate from E1-ACN.

In another embodiment, the present invention provides a method of making form T2RP including the step of heating, at atmospheric pressure, the prior-art sesquihydrate at about 80° to about 150° C., preferably 120° C.

In another embodiment, the present invention provides a method of making hemihydrate T2RP including the step of heating, at atmospheric pressure, novel gatifloxacin form G about 80° to about 130° C., preferably 120° C. to effect the conversion.

In still yet another embodiment, the present invention provides novel crystalline gatifloxacin forms A, B, C, D, E1, F, G, H, I, and J having an average particle size of 100 μm or less, preferably 50 μm or less.

The present invention provides a plurality of particles of any of the gatifloxacin forms A, B, C, D, E1, F, G, H, I, and J having the diameter of all particles in the plurality equal to or less than about 100 μm; preferably, equal to or less than about 50 μm. Particles of the plurality will vary in characteristics and the characteristics of no individual or small proportion of the particles will materially affect the advantages afforded by this invention which may include more rapid dissolution and the potential for improved bioavailability. Rather, the characteristics of the pharmaceutical composition are determined from a statistically significant sampling of the composition and measurement of bulk, or average, properties of the sample. Statistically significant measurements include those with a statistical sampling error of about 2% or less. The "average particle diameter" refers to the equivalent spherical diameter as determined by well-known methods, e.g., laser light scattering method, or sieving methods.

Gatifloxacin of the above-defined defined particle diameter may be produced by known methods of particle size reduction starting with crystals, powder aggregates and coarse powder of gatifloxacin of one or more of crystalline forms A, B, C, D, E1, F, G, H, I, and J. The principal operations of conventional size reduction are milling of a feedstock material and sorting of the milled material by size.

A fluid energy mill, or micronizer, is an especially preferred type of mill for its ability to produce particles of small size in a narrow size distribution. As those skilled in the art are aware, micronizers use the kinetic energy of collision between particles suspended in a rapidly moving fluid (typically air) stream to cleave the particles. The suspended particles are injected under pressure into a recirculating particle stream. Smaller particles are carried aloft inside the mill and swept into a vent connected to a dust collector. The feedstock may be pre-milled to about 150 to 850 µm.

Examples of a useful micronizers include a fluid energy mill such as Microgrinding MC-300 KX, (Microgrinding Ltd., 6995 Molinazzo di Monteggio, CH), Alpine-Hosokawa Fluidized bed opposed jet mill, model AFG (Alpine-Hosokawa, Peter Dorfler Strs., D-8900, DE) and Sturtavent micronizer jet mill (Sturtavent, 348 Circuit St., Hanover, Mass., USA). Alternatively, a pinmill such as Alpine UPZ 160 or similar equipment can be used.

The feed material to the micronizer can have an average PSD about 100-200 microns. The material is fed into the micronization system in a controlled feed rate by means of a screw feeder or a vibratory feeder. The air jet mill is operated with controlled air pressures. For the Microgrinding MC-300 KX, the feed rate is 40-60 kg/hr, the feed air pressure is 6-8.5 bar and the grinding air is 3-6 bar.

The material is fed into the mill system in a controlled feed rate by means of a screw feeder or a vibratory feeder. The mill is operated with controlled speed. For the Alpine UPZ 160, the feed rate is 60-75 kg/hr, the mill speed is 7000-15,000 rpm.

The novel crystalline forms of the present invention, as a plurality of particles of particle size ≦100 µm, especially ≦50 µm, are particularly useful for the preparation of pharmaceutical compositions.

Thus, in still yet a further embodiment, any of the novel crystalline forms of gatifloxacin, forms A, B. C. D. E1. F.G, H, I, or J described hereinabove, alone or in any combination, are formulated into a pharmaceutical composition, preferably an oral solid dosage form or a dosage form for parental administration. Preferably, the crystalline form of the gatifloxacin used in making the pharmaceutical composition has a maximum particle size of 100 µm or less, preferably 50 µm or less.

The pharmaceutical composition can be in the form of a solid oral dosage form (e.g., compressed tablets or capsules), or it can be in the form of a liquid oral dosage form (e.g., a solution or oral suspension). It was found that E1 is also stable in formulations at 30° C. for at least 3 months.

Compressed tablets can be made by dry or wet granulation methods as is known in the art. In addition to the pharmaceutically active agent or drug, compressed tablets contain a number of pharmacologically inert ingredients, referred to as excipients. Some excipients allow or facilitate the processing of the drug into tablet dosage forms. Other excipients contribute to proper delivery of the drug by, for example, facilitating disintegration.

Excipients can be broadly classified according to their intended function. This classification is sometimes arbitrary and it is known that a particular excipient can function in more than one way or serve more than one purpose in a formulation.

Diluents increase the bulk of a solid pharmaceutical composition and may make a pharmaceutical dosage form containing the composition easier for the patient and caregiver to handle. Diluents for solid compositions include, for example, microcrystalline cellulose (e.g., AVICEL®, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate and starch. The dissolution rate of a compacted solid pharmaceutical composition in the patient's stomach may be increased by the addition of a disintegrant to the composition.

Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®) and starch.

Glidants can be added to improve the flow properties of non-compacted solid compositions and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Solid and liquid compositions may also be colored using any pharmaceutically acceptable colorant to improve their appearance and/or facilitate patient identification of the product and unit dosage level.

Of course, wet or dry granulate can also be used to fill capsules, for example gelatin capsules. The excipients chosen for granulation when a capsule is the intended dosage form may or may not be the same as those used when a compressed tablet dosage form is contemplated.

Selection of excipients and the amounts to use may be readily determined by the formulation scientist based upon experience and consideration of standard procedures and reference works in the field.

In liquid pharmaceutical compositions of the present invention, one of GTF forms A, B, C, D, E1, F, G, H, I, and J, or mixtures thereof, and any other solid excipients are dissolved or suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity enhancing agent to improve the mouth-feel of the product and/or coat the lining of the gastrointestinal tract. Such agents include, for example, acacia, alginic acid, bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as gluconic acid, lactic acid, citric acid or acetic acid, sodium gluconate, sodium lactate, sodium citrate or sodium acetate.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. The most suitable route in any given case will depend on the nature and severity of the condition being treated. The dosages can be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs.

The active ingredient and excipients can be formulated into compositions and dosage forms according to methods known in the art.

A composition for tableting or capsule filling can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the active ingredients and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

Capsules, tablets and lozenges and other unit dosage forms may be administered in various dosages depending on the need.

The present invention can be further illustrated with the following non-limiting examples.

EXAMPLES

Example 1 (Form A)

3 g of gatifloxacin were slurried in 20 mL of iso-propanol (IPA). The mixture was slurried at ambient temperature for a slurry time of 24 hours with a magnetic stirrer. The mixture was filtered under vacuum, rinsed with iso-propanol (IPA) (10 mL) and analyzed by XRD analysis and showed to be form A.

Example 2 (Form B):

3 g of gatifloxacin were slurried in 20 mL of 1-butanol. The mixture was stirred at ambient temperature for a slurry time of 24 hours with a magnetic stirrer. Then the mixture was filtered under vacuum, the isolated solid rinsed with 1-butanol (10 mL), and analyzed by XRD analysis.

A second portion of the solid obtained after filtration was dried under vacuum at 50° C. for 24 hours. This resulted in a partially amorphous form B.

Example 3 (Form B):

3 g of gatifloxacin were slurried in 20 mL of EtOH absolute. The mixture was stirred at ambient temperature for a slurry time of 24 hours with a magnetic stirrer. Then the mixture was filtered under vacuum, the isolated solid rinsed with absolute EtOH (10 mL), and analyzed by XRD. The product was partially amorphous form B.

Example 4 (Form C)

3 g of gatifloxacin were slurried in 20 mL of 1-butanol. The mixture was stirred at ambient temperature for a slurry time of 24 hours with a magnetic stirrer. The mixture was then filtered under vacuum, the isolated solid rinsed with 1-butanol (10 mL), and dried at atmospheric pressure in an oven at 60° C. for 24 hours.

Example 5 (Form C)

5 g of gatifloxacin were suspended in 40 mL of 1-butanol. The mixture was heated to reflux temperature until complete dissolution of the material. The solution was then stirred at this temperature for 5 minutes, cooled to ambient temperature, and then to 5° C. The stirring was maintained at this temperature for one hour and then the mixture was filtered under vacuum. The solid obtained was put in an atmospheric oven at 60° C. for 40 hours.

The sample was analyzed by PXRD and found to be form C.

Example 6 (Form D):

3 g of gatifloxacin were slurried in 20 mL of methanol. The mixture was stirred at ambient temperature for a slurry time 24 hours with a magnetic stirrer. Then the mixture was filtered under vacuum, the isolated solid rinsed with methanol (10 mL) and analyzed by XRD.

Example 7 (Form D):

2 g of gatifloxacin were put in a beaker. This beaker was put open in a bottle-containing methanol. Then this bottle was hermetically closed for 15 days, in order to create an atmosphere saturated with methanol vapors. The sample was then analyzed by XRD analysis.

Example 8 (Form F):

5 g of gatifloxacin were put in suspension in 20 mL of a aqueous solution of MeOH 90%. The mixture was heated to reflux temperature and a solution of MeOH 90% (109 mL) was added to complete the dissolution of the material. The solution was then stirred at this temperature for 5 minutes, cooled to ambient temperature, and then to 5° C. The mixture was maintained at this temperature for one hour and then was filtered under vacuum. The sample was analyzed by PXRD, with no further drying, and found to be form F.

Example 9 (Form G):

5 g of gatifloxacin were put in suspension in 20 mL of a aqueous solution of MeOH 90%. The mixture was heated to reflux temperature and a solution of MeOH 90% (109 mL) was added to complete the dissolution of the material. The solution was then stirred at this temperature for 5 minutes, cooled to ambient temperature, and then to 5° C. The mixture was maintained at this temperature for one hour and then was filtered under vacuum. The sample was dried in an atmospheric oven at 60° C. for 24 hours. These samples were analyzed by XRD analysis and found to be form G.

Example 10 (Form H):

3 g of gatifloxacin were slurried in 20 mL of toluene. The mixture was stirred at ambient temperature for a slurry time of 24 hours with a magnetic stirrer. Then the mixture was filtered under vacuum, the isolated solid rinsed with toluene (10 mL). The sample was analyzed by PXRD analysis with no further drying.

Example 11 (Form H):

5 g of gatifloxacin were put in suspension in 50 mL of toluene equipped with a condenser and a Dean-Stark trap. The mixture was heated to reflux until complete dissolution of the material. After 10 minutes of a strong reflux the solution was cooled to ambient temperature, and then to 5° C. The mixture was maintained at this temperature for one hour and then was filtered under vacuum. The sample was analyzed by XRD analysis with no further drying.

Example 12 (Form I):

5 g of gatifloxacin were put in suspension in 40 mL of 1-butanol. The mixture was heated to reflux temperature until complete dissolution of the material. The solution was then stirred at this temperature for 5 minutes, cooled to ambient temperature, and then to 5° C. The stirring was maintained at this temperature for one hour and then the mixture was filtered under vacuum. The sample was analyzed by XRD analysis with no further drying.

Example 13 (Form J):

3 g of gatifloxacin were slurried in 20 mL of technical IPA. The mixture was stirred at ambient temperature for a slurry time of 24 hours with a magnetic stirrer. Then the mixture was filtered under vacuum and the isolated solid rinsed with technical IPA (10 mL). The sample was divided in two portions. The first portion was dried in a vacuum oven at 50° C. for 24 hours and the second portion was dried in an atmospheric oven at 60° C. for 24 hours. These two dried samples were analyzed by XRD analysis and shown to be form J.

Example 14 (Form J):

2 g of gatifloxacin were put in a beaker. This beaker was put open in a bottle-containing isopropanol. Then this bottle was hermetically closed for 15 days in order to create an atmosphere saturated with isopropanol vapors. The sample was then analyzed by XRD analysis.

Example 15 (Form J):

2 g of gatifloxacin were put in a beaker. This beaker was put open in a bottle-containing methylethyl ketone. Then this bottle was hermetically closed for 15 days in order to create an atmosphere saturated with methylethyl ketone vapors. The sample was then analyzed by XRD analysis.

Example 16 (Form J):

3 g of gatifloxacin were slurried in 20 mL of acetone. The mixture was stirred at ambient temperature for a slurry time of 24 hours with a magnetic stirrer. Then the mixture was filtered under vacuum, and the isolated solid rinsed with acetone (10 mL). The sample was divided in two portions. The first portion was not dried and the second portion was dried in a vacuum oven at 50° C. for 24 hours. These two samples were analyzed by XRD analysis and found to be form J.

Example 17 (Form J):

3 g of gatifloxacin were slurried in 20 mL of THF. The mixture was stirred at ambient temperature for a slurry time of 24 hours with a magnetic stirrer. Then the mixture was filtered under vacuum, rinsed with THF (10 mL). The sample was divided in two portions. The first portion was not dried and the second portion was dried in a vacuum oven at 50° C. for 24 hours. These two samples were analyzed by XRD analysis and found to be form J.

Example 18 (Form J):

5 g of gatifloxacin were put in suspension in 30 mL of technical IPA. The mixture was heated to reflux temperature and IPA (39 mL) was added to get the complete dissolution of the material. The solution was then stirred at this temperature for 5 minutes, cooled to ambient temperature, and then to 5° C. The stirring was maintained at this temperature for one hour and then the mixture was filtered under vacuum. The solid was divided in three portions. The first portion was not dried, the second portion was dried in a vacuum oven at 50° C. for 24 hours and the third portion was dried in an atmospheric oven at 60° C. for 24 hours. These three samples were analyzed by XRD analysis and found to be form J.

Example 19 (Form J):

5 g of gatifloxacin were put in suspension in 40 mL of 1-butanol. The mixture was heated to reflux temperature until complete dissolution of the material. The solution was then stirred at this temperature for 5 minutes, cooled to ambient temperature, and then to 5° C. The stirring was maintained at this temperature for one hour and then the mixture was filtered under vacuum. The sample was dried in a vacuum oven at 50° C. for 24 hours and analyzed by XRD analysis and found to be form J.

Example 20 (Form E1-ACN):

Gatifloxacin (20 g) was charged to a 150 mL reactor equipped with a mechanical stirrer and thermometer. Acetonitrile (140 mL) was added and the mixture was heated to 85° C. until a clear solution formed. Hyflow® (5%) was added to the solution and the solution was stirred at 85° C. for 1 hour. A hot filtration was then performed through a jacketed Buchner funnel at 80° C. and the solution was transferred in a clean reactor at 85° C. The solution was then maintained at 85° C. for 5 minutes, then cooled to 60° C. over 30 minutes. At this temperature (seeding temperature) the solution was seeded with gatifloxacin solid, maintained for 1 hour at 60° C. (i.e., seeding time=1 hour), and then cooled to 5° C. over 5 hours. The resulting suspension was then maintained at 5° C. for 1 hour. The mixture was filtered under vacuum. The isolated solid was washed with acetonitrile (15 mL) and dried in a vacuum oven at 50° C. overnight.

The dry sample was analyzed by XRD and found have the characteristic XRD reflections of form E1.

Example 21 (Hydrated E1)

A 1 liter reactor equipped with mechanical stirrer, condenser and thermometer, was charged with gatifloxacin (crude dry; 100 g) and acetonitrile (ACN 1000 mL). The slurry was then heated to reflux (80° C.) and stirred at a rate of 400 rpm. The heating was continued for 0.5 hours until clear solution was obtained.

The clear solution was cooled to 56-58° C. and seeded with 0.1 g of GTF. At the end of the addition the seeded solution was maintained for a seeding time of 2 hours at the seeding temperature of 56-58° C., then cooled over 8 hours to a temperature of 5° C. The temperature was maintained at 5° C., with stirring for 12 hours.

The resulting slurry was filtered (suction) and the collected solid washed with ACN (150 mL) to obtain 91.7 g of wet material.

The wet sample was analyzed by XRD and found to be E1 (Water content by KF=2.48 wt %).

The material obtained was loaded into a Fluidized bed drier and treated at 50° C. for 4 hours with to obtain 84 g of gatifloxacin crystals, form E1 dihydrate.

The sample was analyzed by XRD and found to be E1 (Water content by KF=8.25 wt %).

Example 22 (E1-ACN):

2 g of gatifloxacin were put in a beaker. This beaker was put open in a bottle-containing acetonitrile. Then this bottle was hermetically closed for 15 days in order to create an atmosphere saturated with acetonitrile vapors. The sample was then analyzed by XRD analysis.

Example 23 (Form Ω):

Gatifloxacin (crude, 15 g) was charged to a 250 mL reactor equipped with a mechanical stirrer and thermometer. Acetonitrile (110 mL) was added and the mixture was heated to 85° C. until a clear solution formed. Hyflow® (5%) was added to the solution was stirred at 85° C. for 30 minutes. A hot filtration was then performed through a jacketed Buchner funnel at 80° C. and the solution was charged to a reactor at 85° C. The solution was maintained at 85° C. for 1 h30, then cooled to 55° C. over 1 hour. At 55° C. the solution was seeded with gatifloxacin solid and maintained for 30 minutes at 55° C. The resulting suspension was then cooled to 50° C. over 30 minutes, maintained at this temperature for 30 minutes, cooled to 5° C. over 2 hours, and maintained at 5° C. for 1 hour. The mixture was filtered under vacuum and dried in a vacuum oven at 50° C. overnight.

The dry sample was analyzed by XRD and found to be form Ω.

Example 24 (T2RP):

Form E1 (1 g) was slurried in 6.6 mL of ethanol and stirred at ambient temperature for 2 hours. The slurry was then filtered under vacuum and the collected solid washed with ethanol (3 ml). The washed collected solid was then dried at 50° C. overnight and was analyzed by XRD analysis and shown to be form T2RP.

Example 25 (T2RP):

3 g of dry form Ω were put in a flask equipped with a condenser and a magnetic stirrer. Ethanol (19.8 mL) was added and the slurry was stirred at ambient temperature for 4 hours. A portion of the solid isolated from the slurry was dried at 50° C. under vacuum until constant weight and then was analyzed by XRD. This sample was form T2RP.

Example 26 (Form T2RP Hemihydrate):

A 10 liter reactor equipped with mechanical stirrer, condenser and thermometer, was charged with GTF-Crude dry (1 Kg) and acetonitrile (10 liter). The slurry was then heated to reflux (80° C.) and stirred at a rate of 400 rpm for 2 hours at this temperature to obtain a solution. The solution was filtered. The clear solution was cooled to 56-58° C. and gatifloxacin T2RP hemihydrate (0.1 g) was added.

After seeding, the seeded solution was stirred for a seeding time of 2 hours at the seeding temperature of 56-58° C., cooled to 5° C. over about 8 hours, and maintained with stirring for 2 hours at this temperature. The resulting slurry was filtered under vacuum and the collected solid washed with acetonitrile (1.5 L) to obtain 865.3 g of wet material.

The wet material was charged to a 10 L reactor and EtOH (6 L) was then charged to the reactor. The slurry was stirred at 25° C. for, 24 hours. The slurry was filtered under vacuum and washed with EtOH (1 L).

The wet material was loaded into a fluidized bed apparatus and treated at 50° C. for 4 hours.

After treatment in the fluidized bed drier, the material was found to be form T2RP by XRD analysis.

Example 27 (Hydrated E1):

A 140 liter reactor equipped with mechanical stirrer, condenser and thermometer, was charged with dimethyl sulfoxide (DMSO, 120 L). The DMSO was heated to 55° C. and the reactor was charged with 2-methylpiperazine (8.6 kg). Gatifloxacin acid was charged, in four portions, every 2 hours (3×4=12 Kg). The reaction mixture was stirred at a rate of 110 rpm under nitrogen atmosphere. The temperature was maintained for 24 hours until completion of the reaction. The reaction mixture was cooled to 48° C. and water (24 L) was added at this temperature. The mixture was cooled to 5° C. during 3.5 hours and maintained with stirring for 15 hours at this temperature. The mixture was filtered (suction) and washed with acetonitrile (18 L) to obtain 15.9 Kg of gatifloxacin.

A 140 liter reactor equipped with mechanical stirrer, condenser and thermometer, was charged with the wet product from above (13.3 Kg, 10-20% wetness) and 72 liter of water. The mixture was stirred at 25° C. for 1 hr. The slurry was filtered under vacuum and washed with acetonitrile (21 L) to obtain gatifloxacin wet material (17.5 Kg, about 50% wetness).

A 140 liter reactor equipped with mechanical stirrer, condenser and thermometer, was charged with the wet material from the previous step (8.4 kg) and with acetonitrile (70.9 L). The mixture was then heated to reflux (80° C.) and stirred at a rate of 110 rpm. The heating was continued for 0.5 hours until a clear solution was obtained. The clear solution was cooled to 60° C. and solvent was distilled-off under vacuum (100 mm Hg). After 3 hr, essentially all the solvent was removed. Acetonitrile (49 L) was charged and the mixture was heated to reflux (80° C.). The heating was continued for 0.5 hours until a clear solution was obtained.

The clear solution was filter through a 5, 1, 0.2-micron filter. Then 500 ml of water was added and the clear solution was cooled to 62° C. and gatifloxacin (0.1 gr) was added. After addition, the stirring was maintained for 2 hours at 62° C., then the mixture was cooled during 3 hours to 5° C. and maintained with the stirring for 1 hours at this temperature. The resulting slurry was filtered under vacuum and washed with acetonitrile (5 L) to obtain 5 kg of wet material.

The wet sample was form E1 by PXRD.

A portion of the wet material was loaded into a fluidized bed drier and dried at 25° C. for 6 hours. Gatifloxacin E1 dihydrate was obtained (water content by Karl-Fisher, 9.4%).

Example 28 (E1 Dihydrate):

1 Kg of gatifloxacin form E1 (6.5% water content by KF) was packed into a Fluidized bed drier and treated at 25° C. for 6 hours. Gatifloxacin form E1 dihydrate was obtained (9.4% water content by Karl-Fisher).

Example 29 Interconversion of Forms by Thermal Treatment:

Approximately 200 mg of several of the novel crystalline forms of the present invention, prepared as described in the foregoing examples, and several of the prior-art crystalline forms were subjected to various thermal treatments. The treatments and the results are described in Table II below

TABLE II

XRD results of Gatifloxacin samples before and after heating

| Starting form | Heating conditions | form Obtained |
|---|---|---|
| A | 50° C., 24 h, vacuum or 60 C, 24 h | J |
| B | 50° C., 24 h, vacuum | C |
| F | 50° C., 24 h, vacuum | G |
| G | 120° C., 1 h | Omega[1]. |
| I | 60° C., 24 h, Atmospheric pressure | C |
| J | 120° C., 1 h | omega |
| sesquihydrate | 120° C., 1 h | T2RP + omega |
| Hemihydrate | 120° C., 1 h | T2RP |
| T1RP | 120° C., 1 h | Hemihydrate |

[1]Contains few additional XRD peaks

Example 30

200 mg of gatifloxacin form J were put in 80% relative humidity for 1 week. The resulting sample was analyzed by XRD, TGA and KF. The resulting sample was found to have the crystal structure of the sesquihydrate (LOD=7.8%, KF=6.6%).

Example 31

200 mg of gatifloxacin omega form were put in 80% relative humidity for 1 week, and then analyzed by XRD and by TGA. The resulting sample was found to have sesquihydrate crystal structure (LOD=7.7%).

Example 32

200 mg of gatifloxacin form E1 were heated to 100° C. for 1 hour. The XRD of the resulting sample was that of the omega form.

We claim:

1. A crystalline form E1 of gatifloxacin having the following chemical formula

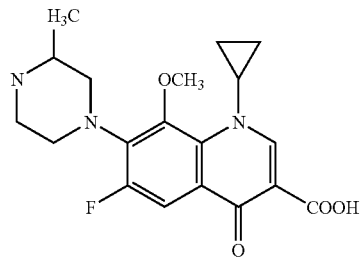

characterized by x-ray reflections at about 7.1°, 7.3°, 10.8°, 15.7°, 16.4°, and 18.1°, ±0.2°2θ.

2. The crystalline form E1 of gatifloxacin of claim 1 containing acetonitrile, water, or mixtures thereof up to about 10% by weight.

3. The crystalline form E1 of gatifloxacin of claim 2, designated E1-ACN, comprising up to about 10% by weight acetonitrile.

4. The crystalline form E1 of gatifloxacin of claim 2, designated E1 hydrate, comprising about 50% to about 10% by weight water.

5. The crystalline form E1 of Gatifloxacin according to claim 1, wherein the crystalline form is a dihydrate.

6. The crystalline form E1 of gatifloxacin of claim 1 having an x-ray diffraction diagram as shown in FIGS. 14a through 14g.

7. A pharmaceutical composition comprising the crystalline gatifloxacin form E1 of claim 1, wherein the gatifloxacin form E1 is a hydrate that is stable against transformation to sesquihydrate when stored at 30° C. and 60% relative humidity for 3 months.

8. The crystalline form E1 of gatifloxacin of claim 2, comprising about 80% to about 10% by weight acetonitrile.

9. The crystalline form E1 of gatifloxacin of claim 4, comprising about 75% to about 10% by weight water.

10. The crystalline gatifloxacin Form E1 -dihydrate of claim 5, comprising about 90% by weight water.

11. A pharmaceutical composition comprising the gatifloxacin of claim 1 and at least one pharmaceutically acceptable excipient.

12. A pharmaceutical composition comprising the gatifloxacin form E1 hydrate of claim 4, wherein the gatifloxacin form E1 hydrate is stable against transformation to sesquihydrate when stored at 30° C. and 60% relative humidity for 3 months.

13. A pharmaceutical composition comprising the gatifloxacin of claim 5 and at least one pharmaceutically acceptable excipient.

* * * * *